US010266490B2

(12) United States Patent
Rosen et al.

(10) Patent No.: US 10,266,490 B2
(45) Date of Patent: Apr. 23, 2019

(54) RADIOPROTECTOR COMPOUNDS

(71) Applicant: GEORGETOWN UNIVERSITY, Washington, DC (US)

(72) Inventors: Eliot M. Rosen, Fairfax, VA (US); Milton Brown, Brookeville, MD (US); Saijun Fan, Bethesda, MD (US); Thomas Walls, Glenside, PA (US); Kathryn E. Ditmer, Alexandrai, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/385,575

(22) PCT Filed: Mar. 14, 2013

(86) PCT No.: PCT/US2013/031385
§ 371 (c)(1),
(2) Date: Sep. 16, 2014

(87) PCT Pub. No.: WO2013/138600
PCT Pub. Date: Sep. 19, 2013

(65) Prior Publication Data
US 2015/0044293 A1    Feb. 12, 2015

Related U.S. Application Data

(60) Provisional application No. 61/611,932, filed on Mar. 16, 2012, provisional application No. 61/624,687, filed on Apr. 16, 2012.

(51) Int. Cl.
| | | |
|---|---|---|
| C07D 209/58 | (2006.01) |
| C07D 407/06 | (2006.01) |
| C07D 207/16 | (2006.01) |
| C07D 209/42 | (2006.01) |
| C07D 209/88 | (2006.01) |
| C07D 307/46 | (2006.01) |
| A61K 31/341 | (2006.01) |
| A61K 31/343 | (2006.01) |
| A61K 31/404 | (2006.01) |
| A61N 5/10 | (2006.01) |
| C07D 207/48 | (2006.01) |
| C07D 209/18 | (2006.01) |
| C07D 307/42 | (2006.01) |

(52) U.S. Cl.
CPC .......... *C07D 209/58* (2013.01); *A61K 31/341* (2013.01); *A61K 31/343* (2013.01); *A61K 31/404* (2013.01); *A61N 5/10* (2013.01); *C07D 207/16* (2013.01); *C07D 207/48* (2013.01); *C07D 209/18* (2013.01); *C07D 209/42* (2013.01); *C07D 209/88* (2013.01); *C07D 307/42* (2013.01); *C07D 307/46* (2013.01); *C07D 407/06* (2013.01); *A61N 2005/1094* (2013.01)

(58) Field of Classification Search
CPC .................................................. C07D 209/58
See application file for complete search history.

(56) References Cited

U.S. PATENT DOCUMENTS

| | | | |
|---|---|---|---|
| 3,838,167 A | 9/1974 | Jones | |
| 5,235,068 A | 8/1993 | Minai et al. | |
| 6,251,932 B1 * | 6/2001 | Reichelt | C07D 209/42 514/414 |
| 8,232,310 B2 * | 7/2012 | Toretsky | C07D 209/38 514/410 |
| 8,957,070 B2 * | 2/2015 | Yasuma | C07D 209/12 514/230.5 |
| 9,045,415 B2 * | 6/2015 | Toretsky | C07D 209/38 |
| 2007/0088071 A1 * | 4/2007 | Kim | C07D 209/08 514/415 |
| 2011/0312979 A1 * | 12/2011 | Li | A61K 31/52 514/263.22 |

FOREIGN PATENT DOCUMENTS

| | | | | |
|---|---|---|---|---|
| JP | WO 2005012245 A1 * | 2/2005 | ........ C07D 207/333 |
| JP | WO 2005082905 A1 * | 9/2005 | .......... A61K 31/443 |
| JP | 2006182668 A * | 7/2006 | |
| JP | WO 2010137351 A1 * | 12/2010 | ............. A61K 31/44 |
| WO | WO 9915501 A1 * | 4/1999 | .......... C07D 209/42 |
| WO | WO 9935130 A1 * | 7/1999 | .......... C07D 209/18 |
| WO | 2007040166 | 4/2007 | |
| WO | WO 2007070892 A2 * | 6/2007 | .......... C07D 209/30 |
| WO | 2008003703 | 1/2008 | |
| WO | 2008051523 | 8/2008 | |
| WO | WO 2010045188 A1 * | 4/2010 | ........... C07D 209/42 |
| WO | 2011163195 | 12/2011 | |

OTHER PUBLICATIONS

Inada et al. Chem. Letters, 1973, 2(11), pp. 1213-1216.*
Taylor et al. J. Med. Chem. (2011), 54(23), 8174-8187.*
Strokes et al. J. Amer. Chem. Soc. (2011), 133(13), 4702-4705.*
Moloney et al. J. Med. Chem. (1999) 42, pp. 2504-2526.*
Herbert, et al. Document No. 152:255275, retrieved from CAPLUS; Feb. 11, 2010.*
Merla, et al. Document No. 149:533919, retrieved from CAPLUS; Nov. 6, 2008.*
Ivashchenko, et al. Document No. 147:486467, retrieved from CAPLUS; Oct. 18, 2007.*
Carballido, et al. Document No. 147:87706, retrieved from CAPLUS; Jun. 29, 2007.*
Lebreton, et al. Document No. 146:27725, retrieved from STN, Dec. 1, 2006.*
Glasspool, et al. Document No. 145:241748, retrieved from STN, Aug. 17, 2006.*
Neitzel, et al. Document No. 144:22719, retrieved from STN, Dec. 2, 2005.*

(Continued)

*Primary Examiner* — Shawquia Jackson
(74) *Attorney, Agent, or Firm* — Kilpatrick Townsend & Stockton LLP

(57) ABSTRACT

Radioprotector compounds including 3,3'-diindolylmethane (DIM) analogs, are provided. Further provided are methods for their use in reducing or preventing radiation damage, killing a tumor cell and protecting a non-tumor cell, and treating cancer.

14 Claims, 16 Drawing Sheets

(56) References Cited

OTHER PUBLICATIONS

Reichert, et al. Document No. 130:267342, retrieved from STN, Apr. 12, 1999.*

Ishikawa, et al. Document No. 120:106753, retrieved from STN; Mar. 5, 1994.*

Cancer and Metastasis Reviews (1998), 17(1), 91-106.*

Science (1999), vol. 286, 531-537.*

Cancer [online], [retrieved on Jul. 6, 2007]. Retrieved from the internet, URL http://www.nlm.nih.gov/medlineplus/cancer.html>.*

McConnell et al., Identification of a PP2A-interacting protein that functions as a negative regulator of phosphatase activity in the ATM/ATR signaling pathway, Oncogene 26, 2007, pp. 6021-6030.

Mell, et al., Pharmacologic normal tissue protection in clinical radiation oncology: focus on amifostine, Expert Opin Drug Metab Toxicol 4(10), 2008, pp. 1341-1350.

Meng et al., Indole-3-carbinol is a negative regulator of estrogen receptor-alpha signaling in human tumor cells, J Nutr. 130, 2000, pp. 2927-2931.

Moiseeva et al., Extended treatment with physiologic concentrations of dietary phytochemicals results in altered gene expression, reduced growth, and apoptosis of cancer cells, Mol Cancer Ther 6, 2006, pp. 3071-3079.

Moulder et al., Hepatic function and drug pharmacokinetics after total body irradiation plus bone marrow transplant, Int J Radiat Oncol Biol Phys. 19(6), 1990, pp. 1389-1396.

Moynahan et al., Brca1 controls homology-directed DNA repair, Mol Cell 4(4), 1999, pp. 511-518.

Müller-Tidow et al., The cyclin A1-CDK2 complex regulates DNA double-strand break repair, Mol Cell Biol. 24(20), 2004, pp. 8917-8928.

Mulvey et al., Interplay of genes regulated by estrogen and diindolylmethane in breast cancer cell lines, Mol Med. 13, 2007, pp. 69-78.

Nachshon-Kedmi et al., Therapeutic activity of 3,3'-diindolylmethane on prostate cancer in an in vivo model, Prostate, 61, 2004, pp. 153-160.

Paulino et al., Normal tissue development, homeostasis, senescence, and the sensitivity to radiation injury across the age spectrum, Semin Radiat Oncol., 20, 2010, pp. 12-20.

Paull et al., A critical role for histone H2AX in recruitment of repair factors to nuclear foci after DNA damage, Curr Biol 10(15), 2000, pp. 886-895.

International Application No. PCT/US2013/031385, International Preliminary Report on Patentability dated Sep. 25, 2014, 10 pages.

International Application No. PCT/US2013/031385, International Search Report & Written Opinion dated Jun. 28, 2013, 13 pages.

Peng et al., Deficiency in the catalytic subunit of DNA-dependent protein kinase causes down-regulation of ATM, Cancer Res., 65, 2005, pp. 1670-1677.

Perona et al., Signaling pathways involved in clinical responses to chemotherapy, Clin. Transl Oncol. 9(10), 2007, pp. 625-633.

Potten et al., Characterization of radiation induced apoptosis in the small intestine and its biological implications, Int J Radiat Biol 65 (1), Jan. 1994, pp. 71-78.

Pouyet et al., Mutant mouse models of oxidative stress, Transgenic Res. 19(2), 2010, pp. 155-164.

Prasanna et al., Normal tissue protection for improving radiotherapy: Where are the Gaps?, Trans! Cancer Res. , 1, 2012, pp. 35-48.

Raffoul et al., Down-regulation of apurinic/apyrimidinic endonuclease 1/redox factor-1 expression by soy isoflavones enhances prostate cancer radiotherapy in vitro and in vivo, Cancer Res 67, 2007, pp. 2141-2149.

Raffoul et al., Radiosensitization of prostate cancer by soy isoflavones, Curr Cancer Drug Targets 7, 2007, pp. 759-765.

Rahman et al., Inhibition of nuclear translocation of nuclear factor-{kappa}B contributes to 3,3'-diindolylmethane-induced apoptosis in breast cancer cells, Cancer Res 65(1), 2005, pp. 364-371.

Rahman et al., Inactivation of NFkappaB by 3,3'-diindolylmethane contributes to increased apoptosis induced by chemotherapeutic agent in breast cancer cells, Mol Cancer Ther 6, 2007, pp. 2757-2765.

Reed et al., Single-dose and multiple-dose administration of indole-3-carbinol to women: pharmacokinetics based on 3,3'-diindolylmethane, Cancer Epidemiol Biomarkers Prey, 15, 2006, pp. 2477-2481.

Reed et al., Single-dose pharmacokinetics and tolerability of absorption-enhanced 3,3'-diindolylmethane in healthy subjects, Cancer Epidemiol Biomarkers Prey, 17(10), 2008, pp. 2619-2624.

Reliene et al., Antioxidants suppress lymphoma and increase longevity in Atm-deficient mice, J Nutr 137(1 Suppl), 2007, pp. 229S-232S.

Riley et al., Free radicals in biology: oxidative stress and the effects of ionizing radiation, Int J Radiat Biol., 65, 1994, pp. 27-33.

Rogakou et al., DNA double-stranded breaks induce histone H2AX phosphorylation on serine 139, J Biol Chem. 273(10), 1998, pp. 5858-5868.

Rogan, The natural chemopreventive compound indole-3-carbinol: state of the science, In Vivo 20, 2006, pp. 221-228.

Rothkamm et al., Pathways of DNA Double-Strand Break Repair during the Mammalian Cell Cycle, Mol Cell Biol 23(18), 2003, pp. 5706-5715.

Saha et al., BRCA1 down-regulates cellular levels of reactive oxygen species, FEBS Lett. 583(9), 2009, pp. 1535-1543.

Saha et al., Transcriptional regulation of the base excision repair pathway by BRCA1, J Biol Chem., 285, 2010, pp. 19092-19105.

Santini, Amifostine: chemotherapeutic and radiotherapeutic protective effects, Expert Opin Pharmacother 2, 2001, pp. 479-489.

Sarkar et al., Cellular signaling perturbation by natural products, Cell Signal. 21 (11), Nov. 2009, pp. 1541-1547.

Shreeram et al., Wip1 phosphatase modulates ATM-Dependent signaling pathways, Mol Cell 23, 2006, pp. 757-764.

Shrivastav et al., Regulation of DNA double-strand break repair pathway choice, Cell Res 18, 2008, pp. 134-147.

Smith et al., DNA-dependent protein kinase and related proteins, Biochem Soc Symp 64, 1999, pp. 91-104.

Soule et al., The chemistry and biology of nitroxide compounds, Free Radic Biol Med. 42(11), 2007, pp. 1632-1650.

Stewart et al., The DNA double-strand break repair gene hMRE11 is mutated in individuals with an ataxia-telangiectasia-like disorder, Cell 99(6), 1999, pp. 577-587.

Sun et al., Endoplasmic reticulum stress as a correlate of cytotoxicity in human tumor cells exposed to diindolylmethane in vitro, Cell Stress Chaperones, 9, 2004, pp. 76-87.

Tamulevicius et al., Homology-directed repair is required for the development of radioresistance during S phase: interplay between double-strand break repair and checkpoint response, Radiat Res. 167(1), 2007, pp. 1-11.

Taylor et al., Ataxia-telangiectasia-like disorder (ATLD)-its clinical presentation and molecular basis, DNA Repair (Amst), 3, 2004, pp. 1219-1225.

Thompson et al., The manganese superoxide dismutase mimetic, M40403, protects adult mice from lethal total body irradiation, Free Radic Res., 44, 2010, pp. 529-540.

Tomlinson et al., Characterization of a breast cancer cell line derived from a germ-line BRCA1 mutation carrier, Cancer Res. 58(15), 1998, pp. 3237-3242.

Uchida et al., A modified fast (4 day) 96-well plate Caco-2 permeability assay, Pharmacol Toxicol Methods 59(1), 2009, pp. 39-43.

Vaghela et al., Development and validation of dissolution procedures, J Appl Pharmaceutical Sci 01(03), 2011, pp. 50-56.

Verhoeven et al., Epidemiological studies on brassica vegetables and cancer risk, Cancer Epidemiology, Biomarkers & Prevention, 5, 1996, pp. 733-748.

Wagemaker, Heterogeneity of radiation sensitivity of hemopoietic stem cell subsets, Stem Cells Suppl. 1, 1995, pp. 257-260.

Wang et al., Activation of nuclear factor kappaB In vivo selectively protects the murine small intestine against ionizing radiation-induced damage, Cancer Res 64, 2004, pp. 6240-6246.

Watters, Oxidative stress in ataxia telangiectasia, Redox Rep, 8, 2003, pp. 23-29.

(56) References Cited

OTHER PUBLICATIONS

Weigelt, et al., Pharmacokinetic evaluation of palifermin for mucosal protection from chemotherapy and radiation, Expert Opin Drug Metab Toxicol. 7(4), 2011, pp. 505-515.
Wu et al., ATM phosphorylation of Nijmegen breakage syndrome protein is required in a DNA damage response, Nature 405(6785), 2000, pp. 477-482.
Wu et al., Evaluation of genotoxicity of Antrodia cinnamomea in the Ames test and the In vitro chromosomal aberration test, In Vivo 25(3), 2011, pp. 419-423.
Xu et al., Involvement of Brca1 in S-phase and G(2)-phase checkpoints after ionizing irradiation, Mol Cell Biol. 21(10), 2001, pp. 3445-3450.
Xu et al., Phosphorylation of serine 1387 in Brca1 is specifically required for the Atm-mediated S-phase checkpoint after ionizing irradiation, Cancer Res. 62(16), 2002, pp. 4588-4591.
Yamamoto et al., In vitro studies on potentiation of cytotoxic effects of anticancer drugs by interferon on a human neoplastic cell line (HeLa), Cancer Lett. 20(2), 1983, pp. 131-138.
Yoshida et al., Chronic doxorubicin cardiotoxicity is mediated by oxidative DNA damage-ATM-p53-apoptosis pathway and attenuated by pitavastatin through the inhibition of Rac1 activity, J Mol Cell Cardiol. 47(5), 2009, pp. 698-705.
Zhang et al., Enhancement of radiation sensitivity of human squamous carcinoma cells by histone deacetylase inhibitors, Radiat Res 161(6), 2004, pp. 667-674.
Zhao et al., Inflammation and chronic oxidative stress in radiation-induced late normal tissue injury: therapeutic implications, Curr Med Chem. 16(2), 2009, pp. 130-143.
Zhong et al., Association of BRCA1 with the hRad50-hMre11-p95 Complex and the DNA Damage Response, Science 285(5428), 1999, pp. 747-750.
Zhong et al., BRCA1 facilitates microhomology-mediated end joining of DNA double strand breaks, J Biol Chem 277, Aug. 2002, pp. 28641-28647.
Zhong et al., Deficient nonhomologous end-joining activity in cell-free extracts from Brca1-null fibroblasts, Cancer Res 62, 2002, pp. 3966-3970.
Golding et al., Improved ATM kinase inhibitor KU-60019 radiosensitizes glioma cells, compromises insulin, AKT and ERK prosurvival signaling, and inhibits migration and invasion, Mol Cancer Ther. 8(10), 2009, pp. 2894-2902.
Goodarzi et al., Autophosphorylation of ataxia-telangiectasia mutated is regulated by protein phosphatase 2A, EMBO J. 23(22), 2004, pp. 4451-4461.
Goodarzi et al., The influence of heterochromatin on DNA double strand break repair: Getting the strong, silent type to relax, DNA Repair (Amst). 9, 2010, pp. 1273-1282.
Gorgoulis et al., Activation of the DNA damage checkpoint and genomic instability in human precancerous lesions, Nature 434(7035), 2005, pp. 907-913.
Graham et al., Diet in the epidemiology of breast cancer, Am J Epidemiol. 116, 1982, pp. 68-75.
Guo et al., ATM activation by oxidative stress, Science 330(6003), 2010, pp. 517-521.
Heath et al., A phase I dose-escalation study of oral BR-DIM (BioResponse 3,3'-Diindolylmethane) in castrate-resistant, non-metastatic prostate cancer, Am J Transl Res, 2(4), 2010, pp. 402-411.
Hickson et al., Identification and characterization of a novel and specific inhibitor of the ataxia-telangiectasia mutated kinase ATM, ATM. Cancer Res 64(24), 2004, pp. 9152-9159.
Higdon et al., Cruciferous vegetables and human cancer risk: epidemiologic evidence and mechanistic basis, Pharmacol Res. 55(3), Mar. 2007, pp. 224-236.
Hong et al., Bcl-2 family-mediated apoptotic effects of 3,3'-diindolylmethane (DIM) in human breast cancer cells, Biochem. Pharmacol 63, 2002, pp. 1085-1097.
Hosseinimehr, Trends in the development of radioprotective agents, Drug Discovery Today 12(19-20), 2007, pp. 794-805.
Huang et al., Identification of human Ether-à-go-go related gene modulators by three screening platforms in an academic drug-discovery setting, Assay Drug Dev Technol. 8(6), 2010, pp. 727-742.
Hugenberg et al., Oxidative Desulfurization-Fluorination of Thioethers. Application for the Synthesis of Fluorinated Nitrogen Containing Building Blocks, Organic and Biomolecular Chemistry, vol. 8, Oct. 2010, pp. 5682-5691.
Iliakis et al., Mechanisms of DNA double strand break repair and chromosome aberration formation, Cytogenet Genome Res., 104, 2004, pp. 14-20.
Itakura et al., Dimerization of the ATRIP protein through the coiled-coil motif and its implication to the maintenance of stalled replication forks, Mol Biol Cell 16(12), 2005, pp. 5551-5562.
Jakob et al., DNA double-strand breaks in heterochromatin elicit fast repair protein recruitment, histone H2AX phosphorylation and relocation to euchromatin, Nucleic Acids Research, vol. 39, No. 15, Apr. 21, 2011, pp. 6489-6499.
Jarosz et al., Enantiospecific reduction of prochiral ketones of aromatic type to optically active alcohols in Nigrospora oryzae culture, Journal of Basic Microbiology, vol. 36, No. 4, 1996, pp. 245-253.
Jeggo et al., Artemis links ATM to double strand break rejoining, Cell Cycle, 4, 2005, pp. 359-362.
Jellinck et al., Ah receptor binding properties of indole carbinols and induction of hepatic estradiol hydroxylation, Biochem Pharmacol., 45, 1993, pp. 1129-1136.
Jin et al., Indole-3-carbinol prevents cervical cancer in human papilloma virus type 16 (HPV16) transgenic mice, Cancer Res. 59, 1999, pp. 3991-3997.
Jones et al., Modelling and PBPK Simulation in Drug Discovery, AAPS J. 11(1), 2009, pp. 155-166.
Jung et al., ATM gene product phosphorylates I kappa B-alpha, Cancer Res. 57(1), 1997, pp. 24-27.
Jung et al., Interstitial gene delivery in human xenograft prostate tumors using titanium metal seeds, Mol Cancer Ther. 3(6), 2004, pp. 655-659.
Jung et al., NF-kappa B signaling pathway as a target for human tumor radiosensitization, Semin Radiat Oncol. 11(4), 2001, pp. 346-351.
Kamal et al., A high-affinity conformation of Hsp90 confers tumour selectivity on Hsp90 inhibitors, Nature 425, 2003, pp. 407-410.
Kanu et al., ATMINistrating ATM signaling: regulation of ATM by ATMIN, Cell Cycle 7(22), 2008, pp. 3483-3486.
Kastan et al., The many substrates and functions of ATM, Nat Rev Mol Cell Biol 1(3), 2000, pp. 179-186.
Katiyar et al., Mechanism of BRCA1-mediated inhibition of progesterone receptor transcriptional activity, Mol Endocrinol. 23(8), 2009, pp. 1135-1146.
Kitagawa et al., Phosphorylation of SMC1 is a critical downstream event in the ATM-NBS1-BRCA1 pathway, Genes Dev. 18(12), 2004, pp. 1423-1438.
Kitagawa et al., The ATM-dependent DNA Damage Signaling Pathway, Cold Spring Harb Symp Quant Biol. 70, 2005, pp. 99-109.
Kojima et al., Chemoprevention of spontaneous endometrial cancer in female Donryu rats by indole-3-carbinol, Cancer Res., 54, 1994, pp. 1446-1469.
Koll et al., HSP90 inhibitor, DMAG, synergizes with radiation of lung cancer cells by interfering with base excision and ATM-mediated DNA repair, Mol Cancer Ther 7, 2008, pp. 1985-1992.
Komarov et al., A chemical inhibitor of p53 that protects mice from the side effects of cancer therapy, Science 285, 1999, pp. 1733-1737.
Kong et al., Histone deacetylase cytoplasmic trapping by a novel fluorescent HDAC inhibitor, Mol Cancer Ther. 10(9), 2011, pp. 1591-1599.
Kong et al., Mammalian target of rapamycin repression by 3,3'-diindolylmethane inhibits invasion and angiogenesis in platelet-derived growth factor-D-overexpressing PC3 cells, Cancer Res 68(6), 2008, pp. 1927-1934.
Konsoula et al., Adamantanyl-histone deacetylase inhibitor H6CAHA exhibits favorable pharmacokinetics and augments prostate cancer radiation sensitivity, Int J Radiat Oncol Biol Phys. Apr. 1, 2011;79(5):1541-8.

(56) References Cited

OTHER PUBLICATIONS

Konsoula et al., In vitro plasma stability, permeability and solubility of mercaptoacetamide histone deacetylase inhibitors, Int Journal Pharm. 361(1-2), 2008, pp. 19-25.
Konsoula et al., Involvement of P-glycoprotein and multidrug resistance associated protein 1 on the transepithelial transport of a mercaptoacetamide-based histone-deacetylase inhibitor in Caco-2 cells, Biol Pharm Bull 32(1), 2009, pp. 74-78.
Konsoula et al., Pharmacokinetics-pharmacodynamics and antitumor activity of mercaptoacetamide-based histone deacetylase inhibitors, Mol Cancer Ther. 8(10), 2009, pp. 2844-2851.
Kouvaris et al., Amifostine: the first selective-target and broad-spectrum radioprotector, Oncologist 12(6), 2007, pp. 738-747.
Kozlov et al., Involvement of novel autophosphorylation sites in ATM activation, EMBO J. 25(15), 2006, pp. 3504-3514.
Krüger et al., ATM is a redox sensor linking genome stability and carbon metabolism, Sci Signal, vol. 4 Issue 167, Apr. 5, 2011, pe 17.
Kuo et al., Gamma-H2AX—a novel biomarker for DNA double-strand breaks, In Vivo 22(3), 2008, pp. 305-309.
Lavin et al., ATM activation and DNA damage response, Cell Cycle 6(8), 2007, pp. 931-942.
Lawenda et al., Should supplemental antioxidant administration be avoided during chemotherapy and radiation therapy?, J Natl Cancer Inst. 100(11), 2008, pp. 773-783.
Le et al., Plant-derived 3,3'-Diindolylmethane is a strong androgen antagonist in human prostate cancer cells, J Biol Chem. 278, 2003, pp. 21136-21145.
Lee et al., A novel ionizing radiation-induced signaling pathway that activates the transcription factor NF-kappaB, Oncogene 17(14), 1998, pp. 1821-1826.
Lee et al., Activation and regulation of ATM kinase activity in response to DNA double-strand breaks, Oncogene 26, 2007, pp. 7741-7748.
Lee et al., ATM activation by DNA double-strand breaks through the Mre11-Rad50-Nbs1 complex, Science 308(5721), 2005, pp. 551-554.
Levitt et al., Caretaker tumour suppressor genes that defend genome integrity, Trends Mol Med 8, 2002, pp. 179-186.
Li et al., Regulation of FOXO3a/beta-catenin/GSK-3beta signaling by 3,3'-diindolylmethane contributes to inhibition of cell proliferation and induction of apoptosis in prostate cancer cells, J Biol Chem 282(29), 2007, pp. 21542-21550.
Lipinski et al., Experimental and computational approaches to estimate solubility and permeability in drug discovery and development settings, Adv Drug Del Rev 46, 2001, pp. 3-26.
Liu et al., Chk1 is an essential kinase that is regulated by Atr and required for the G(2)/M DNA damage checkpoint, Genes Dev. 14, 2000, pp. 1448-1459.
Loehberg et al., Ataxia telangiectasia-mutated and p53 are potential mediators of chloroquine-induced resistance to mammary carcinogenesis, Cancer Res. 67(24), 2007, pp. 12026-12033.
Ma et al., Growth factor signaling pathways modulate BRCA1 repression of estrogen receptor-alpha activity, Mol Endocrinol. 21(8), 2007, pp. 1905-1923.
Macvittie, Therapy of radiation injury, Stem Cells, 15 Suppl 2, 1997, pp. 263-268.
Madgula et al., In vitro metabolic stability and intestinal transport of P57AS3 (P57) from Hoodia gordonii and its interaction with drug metabolizing enzymes, Planta Med. 74, 2008, pp. 1269-1275.
Mallory et al., Protein kinase activity of Tel1p and Mec1p, two Saccharomyces cerevisiae proteins related to the human ATM protein kinase, Proc Natl Acad Sci USA 97(25), 2000, pp. 13749-13754.
Mansour et al., Protective effect of N-acetylcysteine against radiation induced DNA damage and hepatic toxicity in rats, Biochem Pharmacol. 75(3), 2008, pp. 773-780.
Abbott et al., BRCA1 expression restores radiation resistance in BRCA1-defective cancer cells through enhancement of transcriptioncoupled DNA repair, J Biol Chem 274, 1999, pp. 18808-18812.
Abdelrahim et al., 3,3'-Diindolylmethane (DIM) and derivatives induce apoptosis in pancreatic cancer cells through endoplasmic reticulum stressdependent upregulation of DR5, Carcinogenesis 27, 2006, pp. 717-728.
Agbor-Enoh et al., Novel Inhibitor of Plasmodium Histone Deacetylase That Cures P. berghei-Infected Mice, Antimicrobial Agents Chemother 53(3), 2009, pp. 1727-1734.
Aggarwal et al., Molecular targets and anticancer potential of indole-3-carbinol and its derivatives, Cell Cycle, 4, 2005, pp. 1201-1215.
Albright, Computer programs for the analysis of cellular survival data, Radiat Res 112(2), 1987, pp. 331-340.
Ali et al., Requirement of protein phosphatase 5 in DNA-damage-induced ATM activation, Genes Dev 18, 2004, pp. 249-254.
Anderton et al., Pharmacokinetics and tissue disposition of indole-3-carbinol and its acid condensation products after oral administration to mice, Clin Cancer Res. 10, 2004, pp. 5233-5241.
Anderton et al., Physiological modeling of formulated and crystalline 3,3'-diindolylmethane pharmacokinetics following oral administration in mice, Drug Metab Dispos, 32(6), Jun. 2004, pp. 632-638.
Andreassen et al., Chemical radioprotection: a critical review of amifostine as a cytoprotector in radiotherapy, Semin Radiat Oncol 13 (1), Jan. 2003, pp. 67-72.
Bae et al., BRCA1 induces antioxidant gene expression and resistance to oxidative stress, Cancer Research 64, Nov. 1, 2004, pp. 7893-7909.
Bae et al., BRCA1 regulates gene expression for orderly mitotic progression, Cell Cycle 4(11), 2005, pp. 1641-1666.
Bakkenist et al., DNA damage activates ATM through intermolecular autophosphorylation and dimer dissociation, Nature 421(6922), 2003, pp. 499-506.
Ballal et al., BRCA1 localization to the telomere and its loss from the telomere in response to DNA damage, J Biol Chem. 284(52), 2009, pp. 36083-36098.
Bartkova et al., DNA damage response as a candidate anti-cancer barrier in early human tumorigenesis, Nature 434(7035), 2005, pp. 864-870.
Barzilai et al., ATM deficiency and oxidative stress: a new dimension of defective response to DNA damage, DNA Repair (Amst) 1, 2002, pp. 3-25.
Berger et al., Medical management of radiation injuries: current approaches, Occup Med (Lond). 56, 2006, pp. 162-172.
Bradlow et al., Effects of dietary indole-3-carbinol on estradiol metabolism and spontaneous mammary tumors in mice, Carcinogenesis, 12, Sep. 1991, pp. 1571-1574.
Burdelya et al., An agonist of toll-like receptor 5 has radioprotective activity in mouse and primate models, Science 320(5873), 2008, pp. 226-230.
Buscemi et al., Chk2 activation dependence on Nbs1 after DNA damage, Mol Cell Biol. 21(15), 2001, pp. 5214-5222.
Cariveau et al., Characterization of an NBS1 C-terminal peptide that can inhibit ataxia telangiectasia mutated (ATM)-mediated DNA damage responses and enhance radiosensitivity, Mol Pharmacol. 72(2), 2007, pp. 320-326.
Carter et al., Diindolylmethane alters gene expression in human keratinocytes in vitro, J Nutr. 132, 2002, pp. 3314-3324.
Cassatt et al., Effects of dose and schedule on the efficacy of ethyol: preclinical studies, Semin Oncol 30 (6 Suppl 18), 2003, pp. 31-39.
Chakraborty et al., Prevention and repair of DNA damage by selected phytochemicals as measured by single cell gel electrophoresis, J Environ Pathol Toxicol Oncol 23, 2004, pp. 215-226.
Chang et al., 3,3'-Diindolylmethane inhibits angiogenesis and the growth of transplantable human breast carcinoma in athymic mice, Carcinogenesis, 26, 2005, pp. 771-778.
Chen et al., Ataxia telangiectasia mutated (ATM) is essential for DNA-PKcs phosphorylations at the Thr-2609 cluster upon DNA double strand break, J Biol Chem., 282, 2007, pp. 6582-6587.
Chen et al., Indole-3-carbinol and diindolylmethane as aryl hydrocarbon (Ah) receptor agonists and antagonists in T47D human breast cancer cells, Biochem Pharmacol., 51, 1996, pp. 1069-1076.

(56) References Cited

OTHER PUBLICATIONS

Clarke, Issues in experimental design and endpoint analysis in the study of experimental cytotoxic agents in vivo in breast cancer and other models, Breast Cancer Res Treat, vol. 46, issue 2-3, 1997, pp. 255-2788.
Collins et al., The comet assay: topical issues, Mutagenesis 23(3), 2008, pp. 143-151.
Cope et al., Ultraviolet radiation-induced non-melanoma skin cancer in the Crl:SKH1:hr-BR hairless mouse: augmentation of tumor multiplicity by chlorophyllin and protection by indole-3-carbinol, Photochem Photobiol Sci 5, 2006, pp. 499-507.
Cortez et al., Requirement of ATM-dependent phosphorylation of Brca1 in the DNA damage response to double-strand breaks, Science 286, 1999, pp. 1162-1166.
Crespi et al., Microtiter plate assays for inhibition of human, drug-metabolizing cytochromes P450, Anal Biochem 248(1), 1997, pp. 188-190.
Cucinotta et al., Biochemical kinetics model of DSB repair and induction of γ-H2AX foci by non-homologous end joining, Radiat Res., 169, 2008, pp. 214-222.
Czornak et al., Mystery of DNA repair: the role of the MRN complex and ATM kinase in DNA damage repair, J Appl Genet. 49(4), 2008, pp. 383-396.
Dalessandri et al., Pilot Study: Effect of 3, 3'-Diindolylmethane Supplements on Urinary Hormone Metabolites in Postmenopausal Women With a History of Early-Stage Breast Cancer, Nutrition and Cancer, 50(2), 2004, pp. 161-167.
Daniel et al., Multiple autophosphorylation sites are dispensable for murine ATM activation in vivo, J Cell Biol 183, 2008, pp. 777-783.
Davis et al., Genistein induces radioprotection by hematopoietic stem cell quiescence, Int J Radiat Biol 84, 2008, pp. 713-726.
Del Priore, et al., Oral diindolylmethane (DIM): pilot evaluation of a nonsurgical treatment for cervical dysplasia, Gynecol Oncol., 116(3), 2010, pp. 464-467.
Ditch et al., The ATM protein kinase and cellular redox signaling: beyond the DNA damage response, Trends Biochem Sci. 37(1), 2012, pp. 15-22.
Dote et al., Inhibition of hsp90 compromises the DNA damage response to radiation, Cancer Res 66, 2006, pp. 9211-9220.
Dupré et al., Two-step activation of ATM by DNA and the Mre11-Rad50-Nbs1 complex, Nat Struct Mol Biol. 13(5), 2006, pp. 451-457.
Epperly et al., Antioxidant-chemoprevention diet ameliorates late effects of total-body irradiation and supplements radioprotection by MnSOD-plasmid liposome administration, Radiat Res., 175(6), Jun. 2011, pp. 759-765.
Ertl et al., Fast Calculation of Molecular Polar Surface Area as a Sum of Fragment-Based Contributions and its Application to the Prediction of Drug Transport Properties, J Med Chem vol. 43, 2000, pp. 3714-3717.
Fan et al., BRCA1 and BRCA2 as molecular targets for phytochemicals indole-3-carbinol and genistein in breast and prostate cancer cells, British Journal of Cancer, 94, 2006, pp. 407-426.
Fan et al., Low concentrations of diindolylmethane, a metabolite of indole-3-carbinol, protect against oxidative stress in a BRCA1-dependent manner, Cancer Res. 69(15), 2009, pp. 6083-6091.
Fan et al., Role of NF-kappaB signaling in hepatocyte growth factor/scatter factor-mediated cell protection, Oncogene. 24(10), 2005, pp. 1749-1766.
Fan et al., Role of Src signal transduction pathways in scatter factor-mediated cellular protection, J Biol Chem. 284, 2009, pp. 7561-7577.
Fares et al., The potential efficacy of 3,3'-diindolylmethane in prevention of prostate cancer development, Eur J Cancer Prev., 19, 2010, pp. 199-203.
Firestone et al., Indole-3-carbinol and 3-3'-diindolylmethane antiproliferative signaling pathways control cell-cycle gene transcription in human breast cancer cells by regulating promoter-Sp1 transcription factor interactions, J Nutr. 133 (7 Suppl.), 2003, pp. 2448S-2455S.
Firestone et al., Minireview: modulation of hormone receptor signaling by dietary anticancer indoles, Mol Endocrinol., 23(12), 2009, pp. 1940-1947.
Fiscella et al., Wip1, a novel human protein phosphatase that is induced in response to ionizing radiation in a p53- dependent manner, Proc Natl Acad Sci USA 94, 1997, pp. 6048-6053.
Freshwater, Effects of nuclear weapons on the gastrointestinal system, J R Army Med Corps., 150(3 Suppl 1), 2004, pp. 17-21.
Garikapaty et al., 3,3'-Diindolylmethane downregulates pro-survival pathway in hormone independent prostate cancer, Biochem Biophys Res Commun. 340(2), 2006, pp. 718-725.
Gatei et al., Ataxia telangiectasia mutated (ATM) kinase and ATM and Rad3 related kinase mediate phosphorylation of Brca1 at distinct and overlapping sites. In vivo assessment using phospho-specific antibodies, J Biol Chem 276, Feb. 13, 2001, pp. 17276-17280.
Gatei et al., Role for ATM in DNA damage-induced phosphorylation of BRCA1, Cancer Res. 60, 2000, pp. 3299-3304.
Ghose et al., A knowledge-based approach in designing combinatorial or medicinal chemistry libraries for drug discovery, J Combin Chem 1, 1999, pp. 55-68.

\* cited by examiner

RADIOPROTECTOR COMPOUNDS

CROSS-REFERENCE TO PRIORITY APPLICATIONS

This application claims priority to U.S. Provisional Application Nos. 61/611,932, filed Mar. 16, 2012, and 61/624,687, filed Apr. 16, 2012, which are incorporated herein by reference in their entireties.

STATEMENT REGARDING FEDERALLY FUNDED RESEARCH

This invention was made with government support under grant number R01-CA104546 awarded by the National Institutes of Health. The government has certain rights in the invention.

BACKGROUND

Radioprotector agents are used in diagnostic and therapeutic settings to protect normal (e.g., non-cancerous) tissues or structures from radiation damage. These agents are also used as a means of protection in the setting of radiation exposure to the normal population. However, current commercially available radioprotectors are generally too toxic or are insufficiently active to be clinically useful. Furthermore, it is often necessary to administer these agents prior to radiation exposure, which limits the use of these agents to intentional or expected exposures.

SUMMARY

Provided herein are radioprotector compounds. Also provided herein are methods for their use in reducing or preventing radiation damage in a subject, killing a tumor cell and protecting a non-tumor cell, and treating cancer in a subject. A class of compounds described herein includes compounds of the following structure:

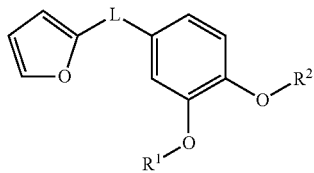

and pharmaceutically acceptable salts or prodrugs thereof. In these compounds, L is —$CH_2$— or —C=O—; and $R^1$ and $R^2$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, or substituted or unsubstituted carbonyl, wherein $R^1$ and $R^2$ can optionally combine to form a heterocycle or heteroaryl. Exemplary compounds according to this structure include:

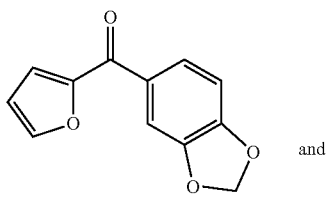

and

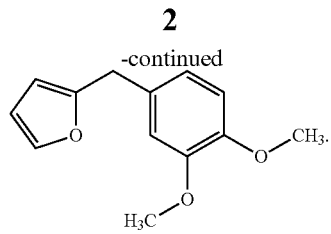

A class of compounds described herein includes compounds of the following structure:

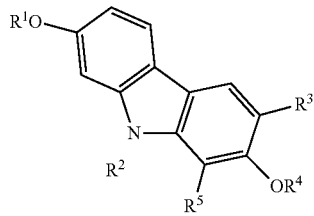

and pharmaceutically acceptable salts or prodrugs thereof. In these compounds, $R^1$ and $R^4$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted carbonyl, or substituted or unsubstituted sulfonyl; $R^2$ is hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkyl, substituted or unsubstituted carbonyl, or substituted or unsubstituted sulfonyl; and $R^3$ and $R^5$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl. In some examples, if $R^1$ is methyl, $R^2$ is H, $R^3$ is H, and $R^5$ is methyl, then $R^4$ is not dansyl. Exemplary compounds according to this structure include:

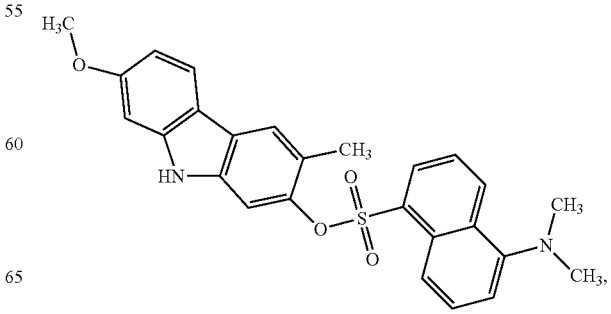

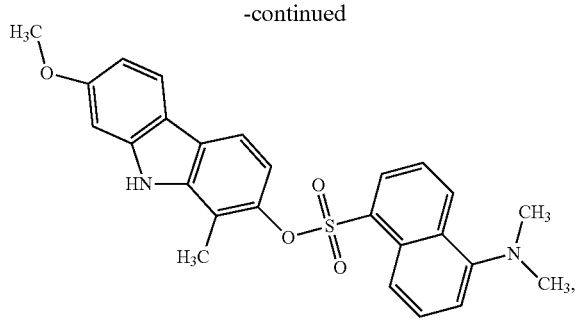

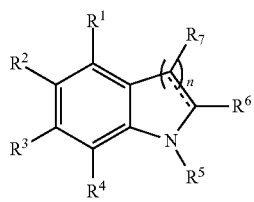

A class of compounds described herein includes compounds of the following structure:

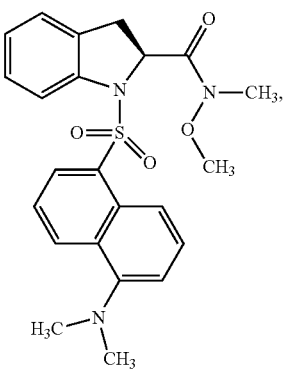

and pharmaceutically acceptable salts or prodrugs thereof. In these compounds, ⚌ is a single or double bond; n is 1, 2, or 3; $R^1$, $R^2$, $R^3$, and $R^4$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; $R^5$ is hydrogen or substituted or unsubstituted sulfonyl; $R^6$ is hydrogen, hydroxyl, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted cycloalkyl, substituted or unsubstituted cycloheteroalkyl, substituted or unsubstituted cycloalkenyl, substituted or unsubstituted cycloheteroalkenyl, substituted or unsubstituted cycloalkynyl, substituted or unsubstituted cycloheteroalkynyl, substituted or unsubstituted aryl, substituted or unsubstituted heteroaryl, substituted or unsubstituted carbonyl, substituted or unsubstituted carboxyl, substituted or unsubstituted sulfonyl, or substituted or unsubstituted phosphinic acid; and each $R^7$ is hydrogen or substituted or unsubstituted alkyl. Exemplary compounds according to this structure include:

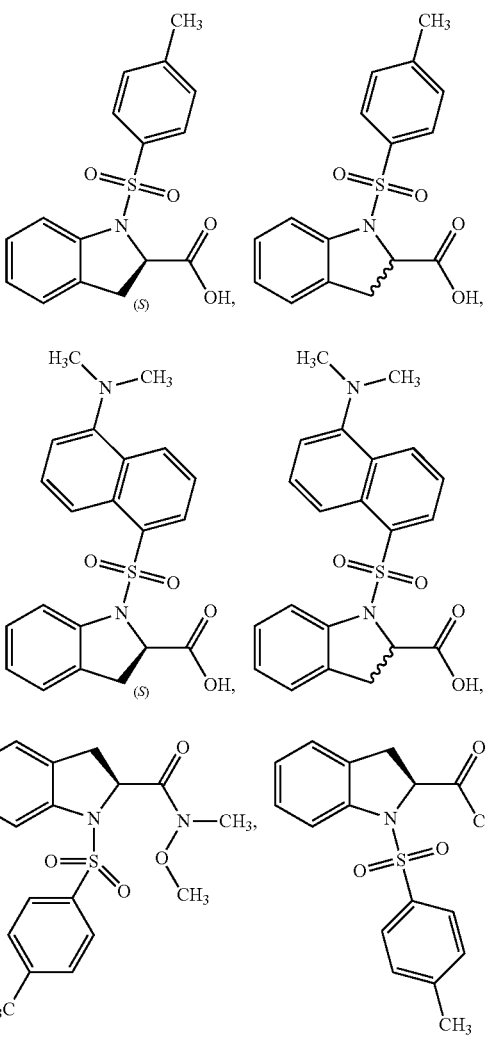

-continued

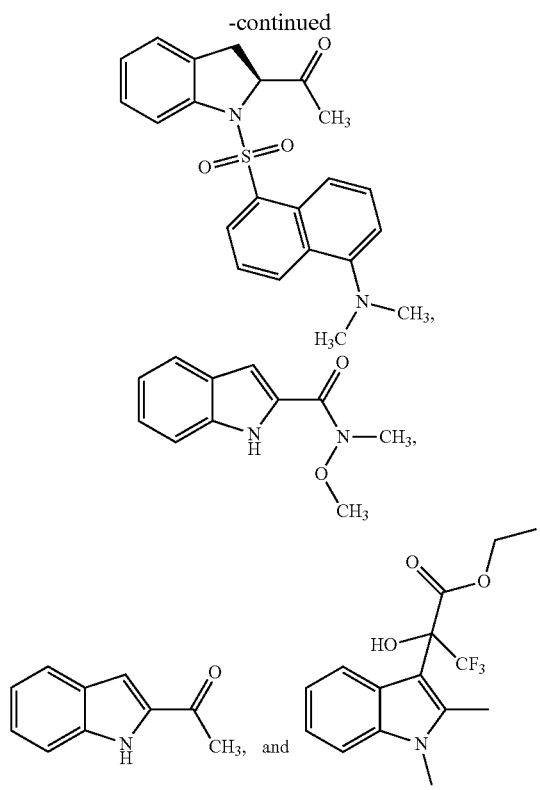

A class of compounds described herein includes compounds of the following structure:

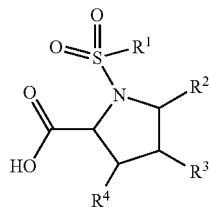

and pharmaceutically acceptable salts and prodrugs thereof. In these compounds, $R^1$ is substituted or unsubstituted aryl; and $R^2$, $R^3$, and $R^4$ are each independently selected from hydrogen, substituted or unsubstituted aryl, and substituted or unsubstituted heteroaryl.

Also provided herein are compositions comprising one or more compounds described above and a pharmaceutically acceptable carrier.

Further provided herein are methods of reducing or preventing radiation damage in a subject. A method of reducing or preventing radiation damage in a subject includes administering to the subject an effective amount of a compound or composition as described herein. Optionally, the method can further include administering a second therapeutic agent, such as a radioprotector compound or 3,3'-diindolylmethane (DIM) to the subject. A method of reducing radiation damage in a subject includes administering to the subject an effective amount of 3,3'-diindolylmethane (DIM) or analog thereof after exposure of the subject to radiation. Optionally, the DIM or analog thereof is administered to the subject at least 24 hours after exposure of the subject to radiation. A method of reducing or preventing radiation damage in a subject includes administering to the subject an effect amount of 3,3'-diindolylmethane (DIM) or analog thereof, wherein the DIM or analog thereof is microencapsulated. Optionally, the DIM or analog thereof is administered in multiple doses.

Also provided herein are methods of killing a tumor cell and protecting a non-tumor cell. A method of killing a tumor cell and protecting a non-tumor cell includes irradiating the tumor cell with an effective amount of ionizing radiation and administering to the non-tumor cell an effective amount of 3,3'-diindolylmethane (DIM), an effective amount of a compound or composition described herein, or a combination thereof. The irradiating step can be performed prior to the administering step. Optionally, the administering step can be performed prior to the irradiating step. Optionally, the method is performed in vivo. Optionally, the method is performed in vitro. The tumor cell can be a $BRCA_1$-deficient tumor cell.

Methods of treating cancer in a subject are also described herein. A method of treating cancer in a subject includes administering to the subject an effective amount of ionizing radiation and administering to the subject an effective amount of 3,3'-diindolylmethane (DIM), an effective amount of a compound or composition described herein, or a combination thereof. Optionally, the cancer is breast cancer (e.g., $BRCA_1$-deficient breast cancer) or ovarian cancer (e.g., $BRCA_1$-deficient ovarian cancer).

The details of one or more embodiments are set forth in the drawings and the description below. Other features, objects, and advantages will be apparent from the description and drawings, and from the claims.

DESCRIPTION OF DRAWINGS

FIG. 5 contains Western blots showing that DIM activates ATM in vivo.

FIG. 7 shows that DIM rapidly causes ATM activation and subsequent phosphorylation of down-stream substrates in cultured cells.

FIG. 11 shows that DIM stimulates DNA repair and inhibits apoptosis.

DETAILED DESCRIPTION

Figure 1:
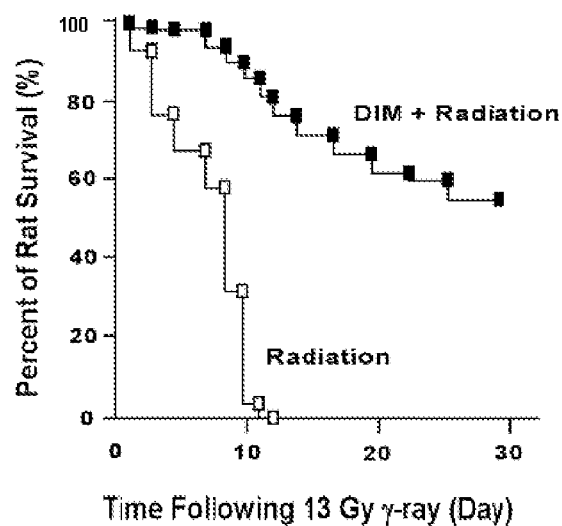
FIG. 1 is a graph demonstrating the percentage of survival for rats that were exposed to total body irradiation and were treated with DIM.

Described herein are compounds for use as radioprotectors. Also provided herein are methods for their use. Such methods include reducing or preventing radiation damage in a subject, killing a tumor cell and protecting a non-tumor cell, and treating cancer in a subject. The methods of reducing or preventing radiation damage in a subject, killing a tumor cell and protecting a non-tumor cell, and treating cancer in a subject described herein include administering to the subject one or more radioprotector compounds.

I. Compounds

A class of radioprotector compounds useful in the methods described herein includes compounds represented by Formula I:

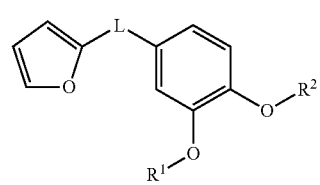

or a pharmaceutically acceptable salt or prodrug thereof.

In Formula I, L is —CH$_2$— or —C=O—.

Also, in Formula I, R$^1$ and R$^2$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, or substituted or unsubstituted carbonyl. Optionally, $R^1$ and $R^2$ can optionally combine to form a heterocycle or heteroaryl.

Examples of Formula I include the following compounds:

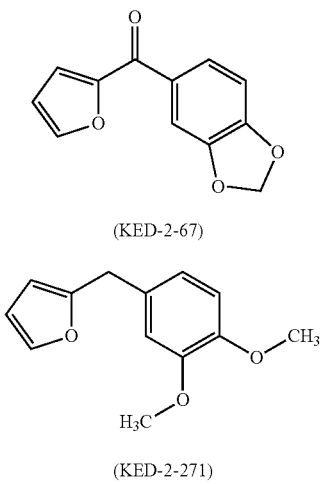

(KED-2-67)

Compound I-1

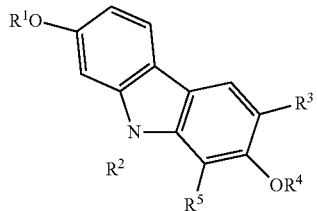

(KED-2-271)

Compoud I-2

A class of radioprotector compounds useful in the methods described herein includes compounds represented by Formula II:

$$\text{II}$$

[Structure of Formula II with $R^1O$, $R^2$, $R^3$, $OR^4$, $R^5$ substituents on carbazole]

or a pharmaceutically acceptable salt or prodrug thereof.

In Formula II, $R^1$ and $R^4$ are each independently selected from hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted carbonyl, or substituted or unsubstituted sulfonyl. Optionally, $R^1$ is methyl. Optionally, $R^4$ is dansyl or benzyl.

Also, in Formula II, $R^2$ is hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkyl, substituted or unsubstituted carbonyl, or substituted or unsubstituted sulfonyl. Optionally, $R^2$ is hydrogen.

Additionally, in Formula II, $R^3$ and $R^5$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl. Optionally, $R^3$ is methyl and $R^5$ is hydrogen. Optionally, $R^3$ is hydrogen and $R^5$ is methyl.

In some examples of Formula II, if $R^1$ is methyl, $R^2$ is H, $R^3$ is H, and $R^5$ is methyl, then $R^4$ is not dansyl.

Examples of Formula II include the following compounds:

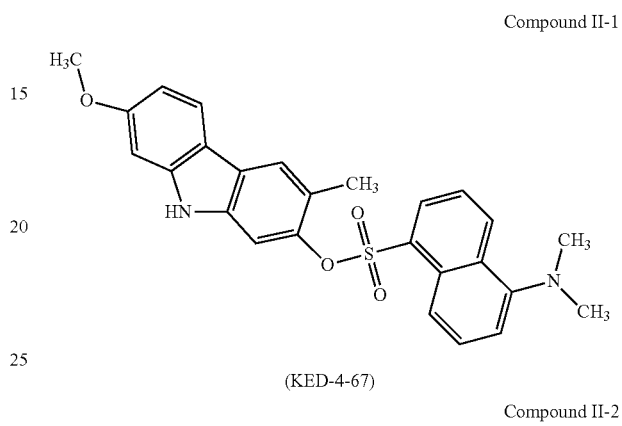

(KED-4-67)

Compound II-1

(KED-4-69)

Compound II-2

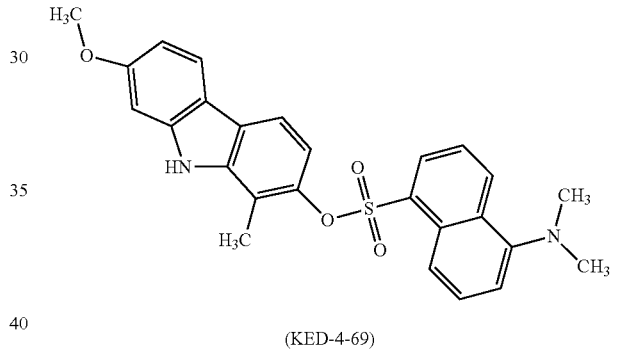

(KED-3-63-2)

Compound II-3

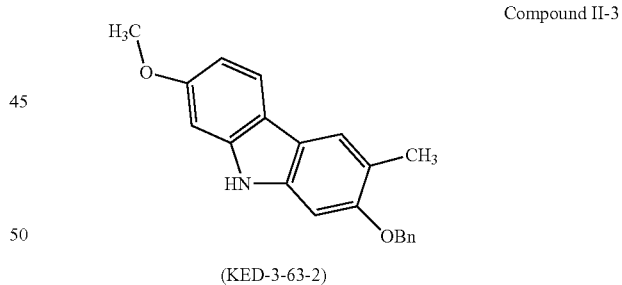

(KED-3-63-1)

Compound II-4

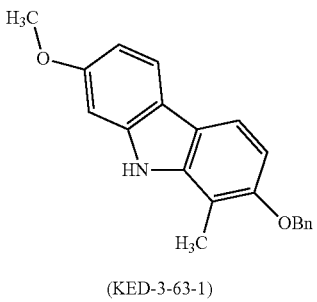

In some examples, the compound of Formula II is not Compound II-2.

A class of radioprotector compounds useful in the methods described herein includes compounds represented by Formula III:

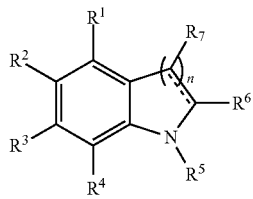

or a pharmaceutically acceptable salt or prodrug thereof.

In Formula III, ----- is a single or double bond.

Also, in Formula III, n is 1, 2, or 3. Optionally, n is 1.

Additionally, in Formula III, $R^1$, $R^2$, $R^3$, and $R^4$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl. Optionally, $R^1$, $R^2$, $R^3$, and $R^4$ are each hydrogen. Optionally, $R^1$, $R^2$, $R^3$, or $R^4$ can be pegylated (e.g., —OPEG).

Further, in Formula III, $R^5$ is hydrogen or substituted or unsubstituted sulfonyl. Optionally, $R^5$ is hydrogen, tosyl, or dansyl.

Additionally, in Formula III, $R^6$ is hydrogen, hydroxyl, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted cycloalkyl, substituted or unsubstituted cycloheteroalkyl, substituted or unsubstituted cycloalkenyl, substituted or unsubstituted cycloheteroalkenyl, substituted or unsubstituted cycloalkynyl, substituted or unsubstituted cycloheteroalkynyl, substituted or unsubstituted aryl, substituted or unsubstituted heteroaryl, substituted or unsubstituted carbonyl, substituted or unsubstituted carboxyl, substituted or unsubstituted sulfonyl, or substituted or unsubstituted phosphinic acid. Optionally, $R^6$ is selected from:

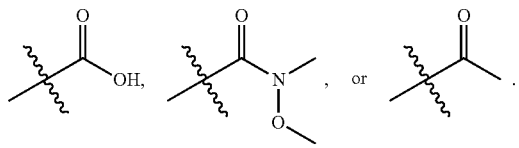

Further, in Formula III, each $R^7$ is hydrogen or substituted or unsubstituted alkyl.

Examples of Formula III include the following compounds:

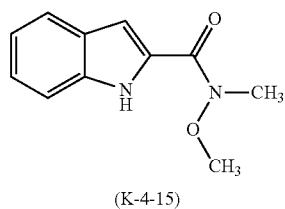

Compound III-1

(K-4-15)

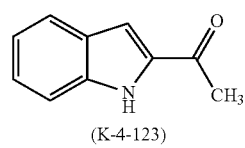

Compound III-2

(K-4-123)

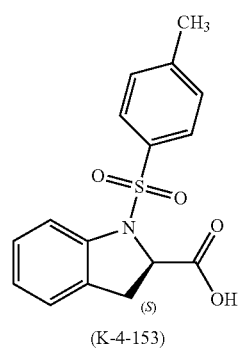

Compound III-3

(K-4-153)

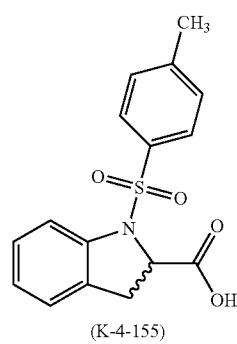

Compound III-4

(K-4-155)

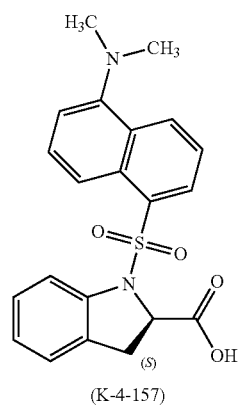

Compound III-5

(K-4-157)

-continued
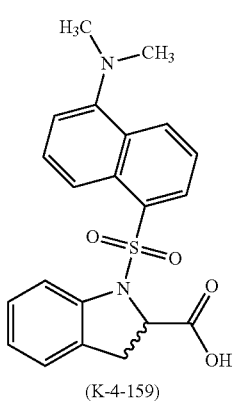
(K-4-159)
Compound III-6
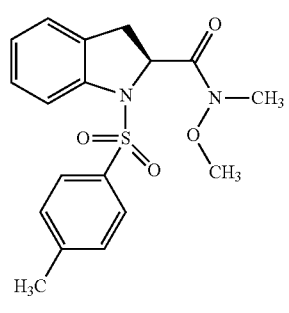
(K-4-23)
Compound III-7
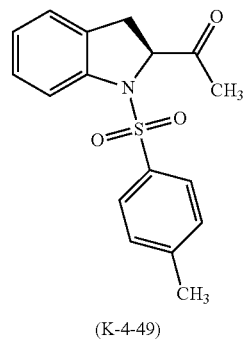
(K-4-49)
Compound III-8
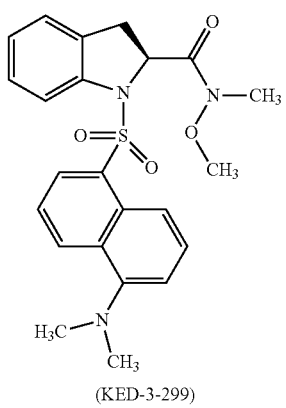
(KED-3-299)
Compound III-9
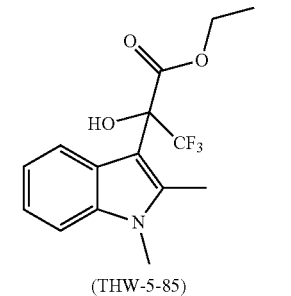
(KED-4-27)
Compound III-10
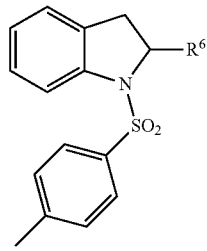
(THW-5-85)
Compound III-11
In some examples, Formula III can be represented by Formula III-A:
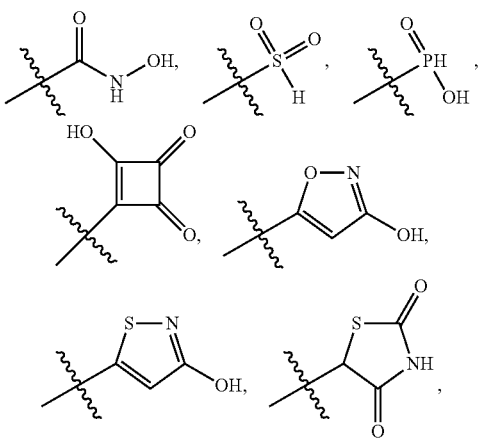
III-A
or a pharmaceutically acceptable salt or prodrug thereof.
In Formula III-A, $R^6$ is selected from hydrogen or one of the following structures:

-continued

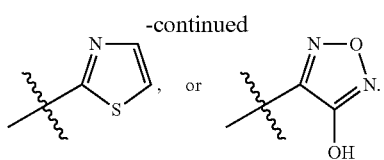

In some examples, Formula III can be represented by Formula III-B:

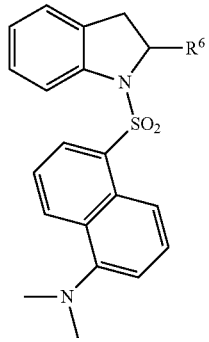
III-B or a pharmaceutically acceptable salt or prodrug thereof.

In Formula III-B, $R^6$ is selected from hydrogen or one of the following structures:

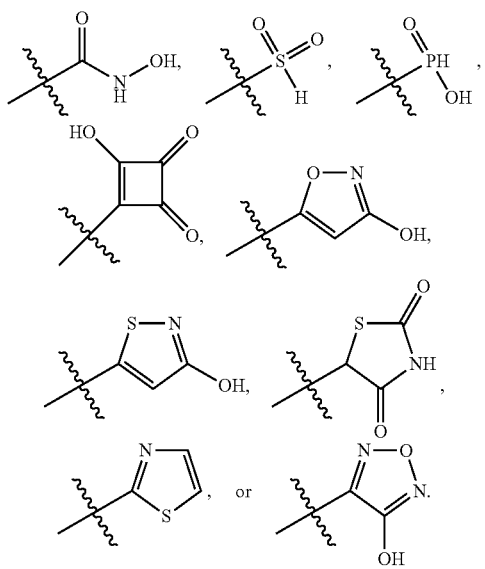

In some examples, Formula III can be represented by Formula III-C:

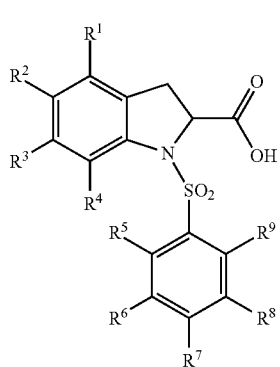
III-C

In Formula III-C, $R^1$, $R^2$, $R^3$, $R^4$, $R^5$, $R^6$, $R^7$, $R^8$, and $R^9$ are each independently selected from hydrogen, fluoro, chloro, methoxy, phenyl, trifluoromethyl, and dimethylamino In some examples, Formula III can be represented by Formula III-D:

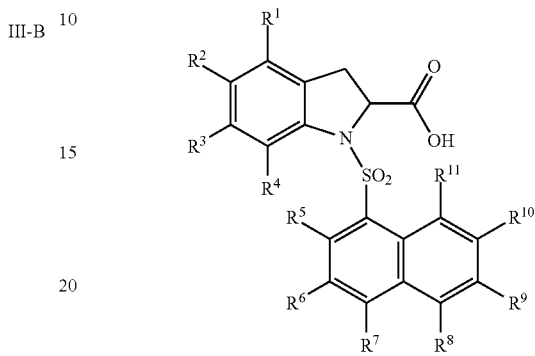
III-D

In Formula III-D, $R^1$, $R^2$, $R^3$, $R^4$, $R^5$, $R^6$, $R^7$, $R^8$, $R^9$, $R^{10}$, and $R^{11}$ are each independently selected from hydrogen, fluoro, chloro, methoxy, phenyl, trifluoromethyl, and dimethylamino. Optionally, $R^8$ is dimethylamino A class of radioprotector compounds useful in the methods described herein includes compounds represented by Formula IV:

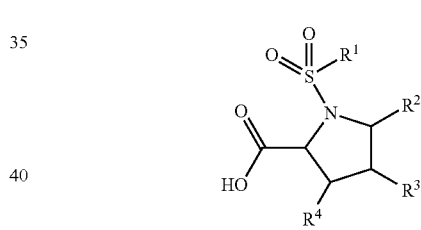
IV or a pharmaceutically acceptable salt or prodrug thereof.

In Formula IV, $R^1$ is substituted or unsubstituted aryl.

Also, in Formula IV, $R^2$, $R^3$, and $R^4$ are each independently selected from hydrogen and substituted or unsubstituted aryl or heteroaryl.

A compound useful in the methods described herein includes 3,3'-diindolylmethane (DIM) as shown below:

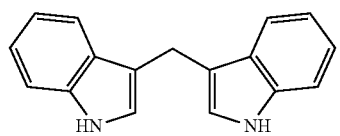

3,3'-diindolylmethane (DIM)

In some examples, the DIM is microencapsulated.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane (—$(CH_2)_9$—$CH_3$).

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

III. Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, Formula III, and Formula IV include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The compounds described by Formula I can be made, for example, using reactions shown in Schemes 1 and 2:

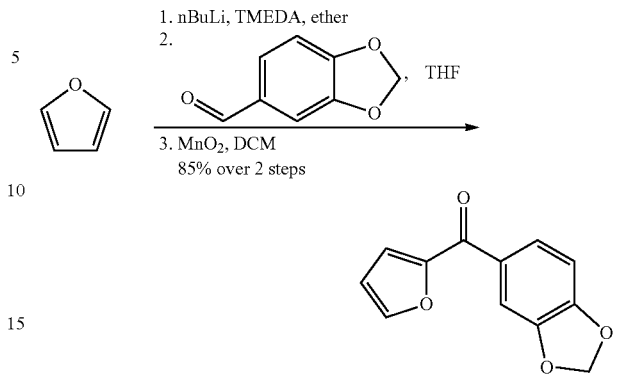

As shown above in Schemes 1 and 2, the synthesis of Compound I-1 and Compound I-2 began with the deprotonation of furan with t-butyl lithium followed by addition into an aryl aldehyde. The resulting alcohol was then oxidized to a ketone using manganese dioxide. For Compound I-2, the carbonyl was reduced using lithium aluminum hydride (LAH).

The compounds described by Formula II can be made, for example, using reactions shown in Scheme 3:

Scheme 3:

-continued

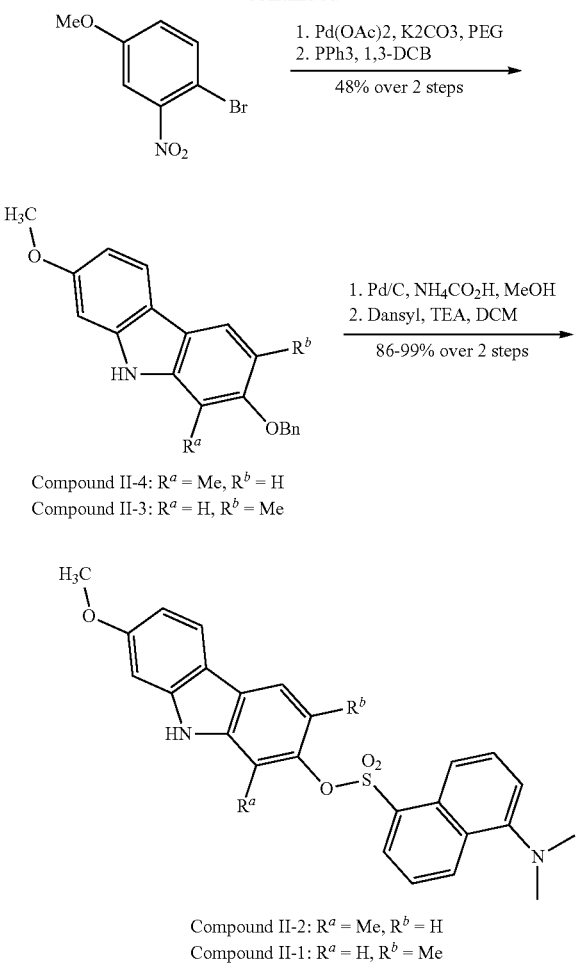

Compound II-4: $R^a$ = Me, $R^b$ = H
Compound II-3: $R^a$ = H, $R^b$ = Me

Compound II-2: $R^a$ = Me, $R^b$ = H
Compound II-1: $R^a$ = H, $R^b$ = Me

As shown above in Scheme 3, Compounds II-1, II-2, II-3, and II-4 were synthesized by benzyl protecting 4-iodophenol, coupling the resulting product with 4-bromo-3-nitroanisole, and then cyclizing the coupled product using triphenylphosphine to provide Compounds II-4 and II-3. The compounds were deprotected using palladium on carbon and then dansylated in the presence of triethylamine in dichloromethane to provide Compounds II-2 and II-1.

The compounds described by Formula III can be made, for example, using reactions shown in Schemes 4-7:

Scheme 4:

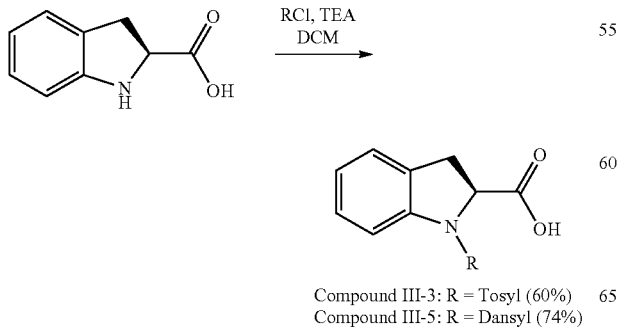

Compound III-3: R = Tosyl (60%)
Compound III-5: R = Dansyl (74%)

Scheme 5:

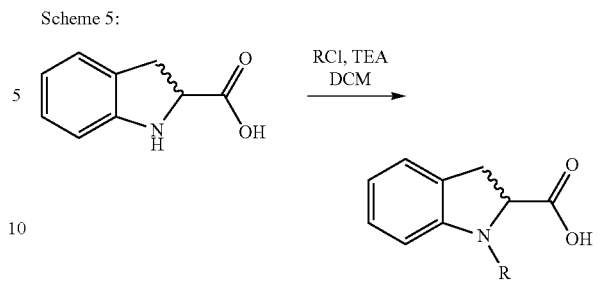

Compound III-4: R = Tosyl (73%)
Compound III-6: R = Dansyl (77%)

Scheme 6:

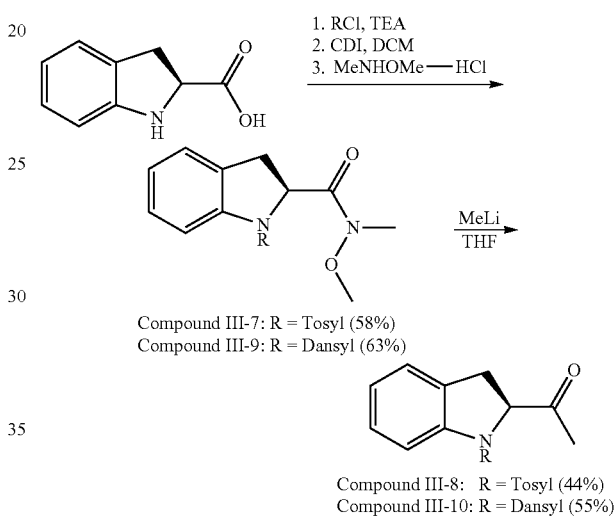

Compound III-7: R = Tosyl (58%)
Compound III-9: R = Dansyl (63%)

Compound III-8: R = Tosyl (44%)
Compound III-10: R = Dansyl (55%)

Scheme 7:

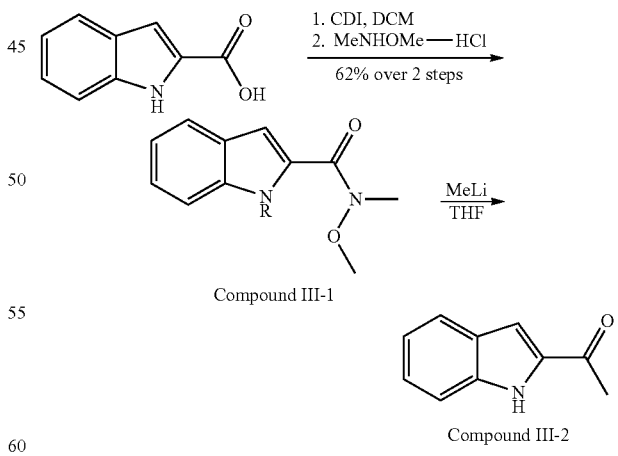

Compound III-1

Compound III-2

As shown above in Schemes 4 and 5, Compounds III-3, III-4, III-5, and III-6 were synthesized from commercially available racemic or (S)-indoline-2-carboxylic acid. Specifically, the hydrogen on the indoline nitrogen was substituted for a tosyl or dansyl group in the presence of triethylamine (TEA) in dichloromethane (DCM). Compounds III-7 and III-9 were also synthesized from (S)-indoline-2-carboxylic acid by substituting the hydrogen on the indoline nitrogen for either a tosyl or dansyl group, and then converting the carboxylic acid to the Weinreb amide after activating with carbonyl diimidazole (CDI). Compounds III-8 and III-10 were prepared from Compounds III-7 and III-9, respectively, by adding methyl lithium (MeLi) in tetrahydrofuran (THF). Following similar procedures, indole-2-carboxylic acid was used to synthesize Compound III-1, which was then treated with methyl lithium in THF to form Compound III-2.

IV. Methods of Use

Provided herein are methods to reduce or prevent radiation damage in a subject. The methods include administering to a subject an effective amount of one or more of the compounds or compositions described herein, or a pharmaceutically acceptable salt or prodrug thereof. The expression "effective amount," when used to describe an amount of compound in a method, refers to the amount of a compound that achieves the desired pharmacological effect or other effect, for example, an amount that results in a reduction to radiation damage to tissue. The compounds and compositions described herein or pharmaceutically acceptable salts thereof are useful for reducing or preventing radiation damage in humans, including, without limitation, pediatric and geriatric populations, and in animals, e.g., veterinary applications.

Further described herein is a method for treating cancer in a subject. The method includes administering to the subject an effective amount of ionizing radiation and then administering to the subject an effective amount of a compound or composition as described herein (e.g., a compound according to one or more of Formula I, Formula II, Formula III, Formula IV, DIM, or microencapsulated DIM). Optionally, the compound according to one or more of Formula I, Formula II, Formula III, or Formula IV is microencapsulated. Optionally, the cancer is breast cancer, such as $BRCA_1$-deficient breast cancer. Optionally, the cancer is ovarian cancer, such as $BRCA_1$-deficient breast cancer. Optionally, the compound or composition can be administered to the subject before or after the subject has been exposed to radiation. For example, the compound or composition can be administered to the subject 1 minute or more, 2 minutes or more, 5 minutes or more, 10 minutes or more, 15 minutes or more, 30 minutes or more, 45 minutes or more, 1 hour or more, 2 hours or more, 3 hours or more, 4 hours or more, 5 hours or more, 10 hours or more, 15 hours or more, 20 hours or more, or 24 hours or more after exposure. Optionally, the compound or composition can be administered in multiple doses.

The methods of reducing or preventing radiation and treating cancer in a subject can further comprise administering to the subject a therapeutic agent. Thus, the provided compositions and methods can include one or more additional agents. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents and radioprotector compounds. The therapeutic agent can, for example, be a chemotherapeutic agent. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, Amifostine.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer or before radiation exposure), during early onset (e.g., upon initial signs and symptoms of cancer or radiation exposure), or after the development of cancer or exposure to radiation. Prophylactic administration can occur for several days to years prior to the manifestation of symptoms of cancer or prior to radiation exposure. Therapeutic treatment involves administering to a subject a therapeutically effective amount of the compounds and compositions or pharmaceutically acceptable salts thereof as described herein after cancer is diagnosed or radiation exposure is identified.

The methods and compounds described herein are also useful in killing a tumor cell and protecting a non-tumor cell. The methods include irradiating the tumor cell with an effective amount of ionizing radiation and administering to the non-tumor cell an effective amount of a compound or composition as described herein. Optionally, the tumor cell is a $BRCA_1$-deficient tumor cell. The irradiating step can be performed prior to the administering step or the administering step can be performed prior to the irradiating step. Optionally, the method is performed in vivo. Optionally, the method is performed in vitro.

The methods herein for prophylactic and therapeutic treatment optionally comprise selecting a subject with or at risk of being exposed to radiation (e.g., military personnel or the civil population under a heightened security due to terrorist threats).

V. Kits

Also provided herein are kits for reducing or preventing radiation damage in a subject or for treating cancer in a subject. A kit can include any of the compounds or compositions described herein. For example, a kit can include 3,3'-diindolylmethane (e.g., microencapsulated DIM), a compound of Formula I, Formula II, Formula III, Formula IV, or combinations thereof. Optionally, the compound according to one or more of Formula I, Formula II, Formula III, and Formula IV is microencapsulated. A kit can further include one or more additional agents, such as anti-cancer agents (e.g., Amifostine). A kit can include an oral or intraperitoneal formulation of any of the compounds or compositions described herein. A kit can additionally include directions for use of the kit (e.g., instructions for treating a subject), a container, a means for administering the compounds or compositions (e.g., a syringe), and/or a carrier.

As used herein the terms treatment, treat, or treating refer to a method of reducing one or more symptoms of a disease or condition. Thus, in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control (e.g., untreated) level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: DIM as a Radioprotector—Cultured Cells Studies

DIM, a metabolite of indole-3-carbinol and a proposed cancer agent, is a potent radiation protector in cultured cells and in rodents (mice and rats). The preparation of DIM that was used for most experiments was a microencapsulated form of DIM produced by BioResponse Nutrients (Boulder, Colo.). This microencapsulated form of DIM is designed with specific excipients (e.g., alpha-tocopherol succinate and phosphatidylcholine) to provide enhanced absorption and, therefore, enhanced bioavailability. In cultured cells, both enhanced absorption DIM and crystalline DIM work very well as radioprotectors, but in animals, the enhanced absorption DIM is a better radioprotector than crystalline DIM, probably, in part, due to greater bioavailability. In various types of cultured (e.g., fibroblasts and epithelial cells), DIM strongly protects against ionizing radiation (Cs-60 gamma radiation or high energy X-rays), based on rigorously performed clonogenic survival assays.

Not to be bound by theory, a mechanism of action is that DIM, in the absence of any DNA damage, appears to hyper-activate the cellular DNA damage-response machinery [including signaling from the "MRN complex" (a trio of proteins involved in DNA damage sensing) to ATM (ataxia-telangiectasia mutated) to BRCA1, CHK1, p53 and other DNA damage response and repair factors]. This leads to enhanced cellular capacity to repair DNA damage. DIM also stimulates the activity of DNA-dependent protein kinase (DNA-PK), another protein involved in the repair of double-strand DNA breaks. Although these are probably not the only mechanisms by which DIM works, they appear to be involved in the radioprotection by DIM. These mechanisms are unique for a radioprotector, because most existing compounds that are radioprotectors do not work by modifying the biological response of cells to radiation, as does DIM. DIM-mediated radioprotection is observed at high doses of radiation as well as low doses (less that 200 cGy); thus DIM works throughout a wide spectrum of radiation doses. Fold-protection of different doses of DIM are in the range of 20 to 100-fold or higher. Data showing DIM radiation protection of cultured cells are provided in the attached grant proposals.

Example 2: DIM as a Radioprotector

The activity for DIM as a radioprotector and a mitigator of radiation damage, via stimulation of an ATM signaling cascade, is demonstrated herein. DIM causes activation of ATM signaling without itself causing DNA damage.

Materials and Methods

Cells Lines and Culture

BRCA1-deficient mouse embryonic fibroblasts (MEFs) and wild-type MEFs were obtained. 184A1 and Hs578Bst cells were cultured. MCF-7 and T47D cells were grown in DMEM plus 5% fetal calf serum, 1-glutamine (5 mM), non-essential amino acids (5 mM), penicillin (100 U/ml), and streptomycin (100 µg/ml) (all obtained from BioWhittaker, Walkersville, Md.).

Reagents

A bioavailable formulation of 3,3'-diindolylmethane (BR-DIM) was obtained from Bioresponse (Boulder, Colo.). BR-DIM is a microencapsulated preparation that has increased oral bioavailability than unformulated crystalline DIM. It is herein referred to as "DIM".

Radiation Survival Curves

Following the indicated treatment(s), subconfluent proliferating cells were irradiated with different doses of $^{137}$Cs γ-rays, harvested using trypsin, and plated at different densities in the absence or presence of DIM (as indicated) for colony formation (clonogenic survival) assays, as described in Zhang et al., Radiat Res, 161:667-674 (2004). Values of surviving fraction are means±SEMs of triplicate plates.

siRNA Treatment

Proliferating cells were treated with gene-specific siRNA or control-siRNA using siRNA Transfection Reagent (Santa Cruz Biotechnology, Santa Cruz, Calif.). ATM-siRNA (sc-29761), BRCA1-siRNA (sc-29219), and control-siRNA (sc-37007) were purchased from Santa Cruz. The cells were exposed to the indicated siRNA (50 nM) for at least 48 hr; and the efficacy of the knockdown was confirmed by Western blotting.

DNA Repair and Apoptosis Assays
  Comet Assays.
  Following the indicated treatment, neutral or alkaline comet assays were performed.
  DNA Strand Rejoining Assay.
  After the indicated cell treatment(s), nuclear lysates were prepared and aliquots of lysate (50 or 75 μg of nuclear protein) were tested for their ability to rejoin a plasmid (pEGFP-1, Clontech) that had been linearized using restriction enzyme SmaI. The reaction products were detected by Southern blotting, which was performed with a digoxigenin-labeled enhanced green fluorescent protein RNA probe. The percent rejoined plasmids 98984 was determined by densitometric quantification of the bands corresponding to rejoined and unrejoined plasmid.

Western Blotting
  Western blotting was performed. The primary antibodies were as follows: rabbit polyclonal anti-BRCA1 (sc-642, Santa Cruz); mouse monoclonal α-actin (sc-1616, Santa Cruz); anti-phospho-BRCA1 (S1387) [AB3257, Millipore (Billerica, Mass.)]; mouse monoclonal anti-ATM (sc-73615, Santa Cruz,); anti-phospho-ATM (S1981); anti-CHK2 (05-649, mouse monoclonal, Millipore); anti-phosph-CHK2 (T68) (ab32055, rabbit monoclonal, Abcam, Cambridge, Mass.); anti-p53 (ab2433, rabbit polyclonal, Abcam), and rabbit polyclonal anti-phospho-p53 (S15) (ab38497, Abcam).

Animal Experiments
  Studies utilized Sprague-Dawley rats (age 12-16 weeks, weight 200±30 g) or C57BL/6 mice (6-8 weeks, ca. 20 g). Animals were administered DIM or carrier (physiological saline) by intraperitoneal injection at the doses and schedules indicated, subjected to total body irradiation using $^{60}$Co γ-rays (0.96 Gy/min), and followed for survival up to 30 days. Mice that either appeared to be moribund or died were considered not to have survived.

Statistical Methods
  For in vivo studies, animal survival was plotted using Kaplan-Meier statistics; and the survival curves were compared using the log-rank test. Other statistical comparisons were made using two-tailed t-tests.

Results
In Vivo Radiation Protection and Mitigation by DIM
  In rats and mice, DIM very potently protects against very high (supra-lethal) doses of radiation: doses so high (e.g., 13-Gy) that, in the absence of DIM, none of the animals survive past 10-days. Female Sprague-Dawley rats (age 12-16 weeks; weight 200±30 gm) were randomized into two groups of 30 animals each, one of which received 13-Gy $^{60}$CO γ-rays (0.96-Gy/min) as a single dose plus 0.1-mL physiological saline intraperitoneally and the other of which received 13-Gy $^{60}$CO γ-rays plus DIM (7.5 mg/kg body weight, ip). Both groups received daily ip injections of 0.1-mL starting 1 day before irradiation and ending 10 days after irradiation. Survival was monitored for 30 days, and the results were plotted using Kaplan-Meier statistics. At a dose of 13-Gy of total body irradiation (TBI), survival of DIM-treated animals is as high as 50-60% at 30 days (see FIG. 1). At lower doses of TBI, the survival of DIM-treated animals was corresponding higher. Radioprotection by DIM was dependent upon the dose of DIM utilized, the timing of administration relative to the TBI, and the number of times DIM was administered (see below). In these experiments, DIM was administered by intraperitoneal injection for convenience, but previous studies indicate excellent biodistribution when DIM (BR-DIM) is given orally. DIM can be given to mice by oral gavage at 250 mg/kg with no toxicity and wide tissue distribution.

Figure 2:
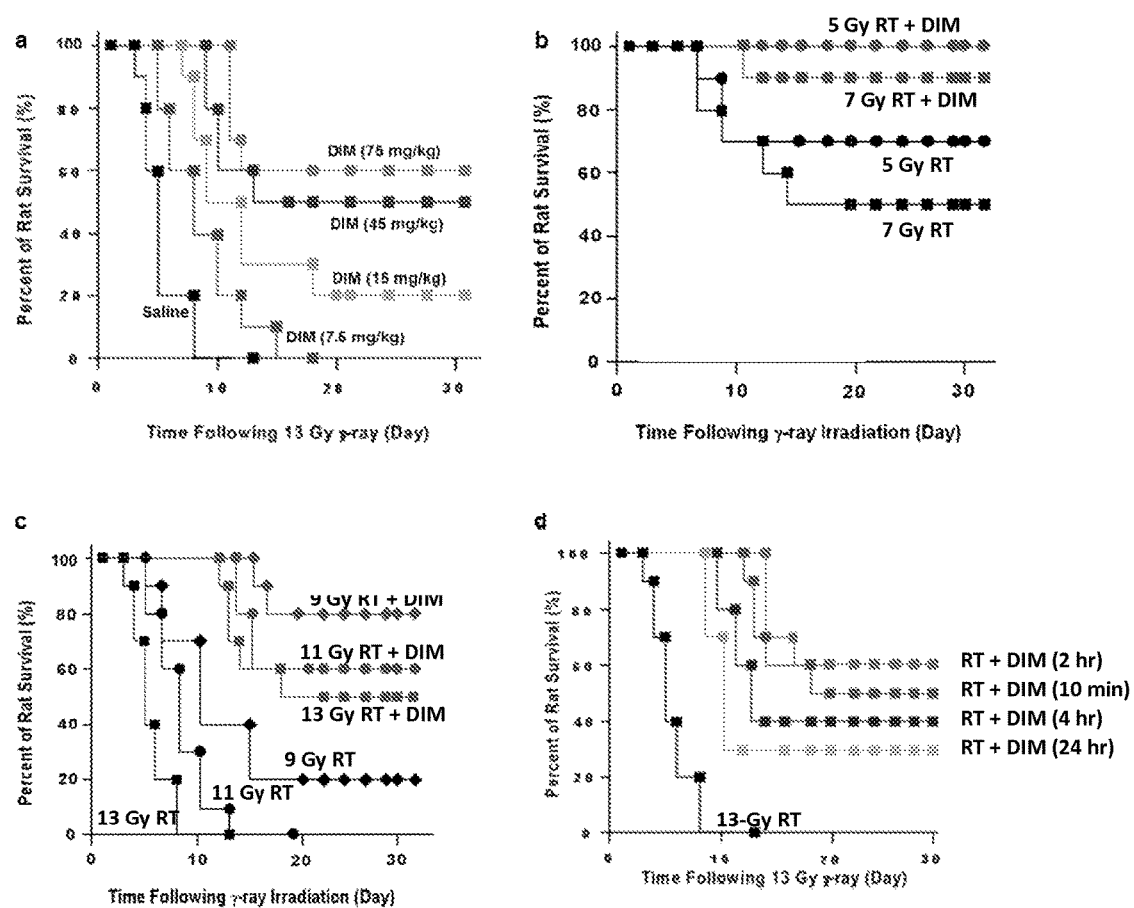
FIG. 2 contains graphs demonstrating the percentage of survival for rats that were exposed to different doses of total body irradiation (RT), with and without DIM treatment. Panel A shows the results for rats exposed to 13-Gy of γ-rays and then given once daily doses of DIM (as indicated) for 14-days, with the first administration 10-min after RT. Panels B and C show the results for rats exposed to different doses of RT and then given once daily doses of DIM (75 mg/kg) for 14-days, with the first administration 10-min after RT. Panel D shows the results for rats given a 13-Gy dose of RT and having DIM (75 mg/kg) administered starting at different times post total body irradiation, as indicated. DIM was administered by intraperitoneal (ip) injection with physiological saline as the vehicle and control animals were irradiated but received injections of saline only. Survival was plotted by Kaplan Meier method.

FIG. 2a shows dose-dependent protection of Sprague-Dawley (SD) rats given once daily injections of DIM for 14-days starting 10-min after a 13-Gy dose of TBI. Here, control animals all died before day 10, while the 30-day survival rates were 60%, 50%, 20%, and 0% when the doses of DIM were 75, 45, 15, and 7.5 mg/kg, respectively. When the first DIM dose was given 24 hours prior to TBI (13-Gy), a much lower daily dose of DIM (7.5 mg/kg) yielded high survival (55%) at 30 days (P<0.001, log-rank test). Thus, if one DIM dose can be given before radiation, protection can be achieved with a very low dose of DIM. DIM similarly protected C57BL/6 mice against TBI, indicating that protection is not species-specific.

In another study, different TBI doses were given followed by once daily DIM injections (75 mg/kg for 14-days starting 10-min post TBI). DIM conferred large increases in survival at each radiation dose (FIGS. 2b and 2c). From these data, the dose-modifying factor (DMF) for DIM (ie., the ratio of $LD_{50/30}$ values (+) vs (−) DIM) administered shortly after radiation is estimated to be 1.9. Using a single TBI dose of 13-Gy and variable timing for the first injection of DIM, survival at 30-days was 50%, 60%, 40%, and 30%, respectively, when the first DIM dose was given 10-min, 2-hr, 4-hr, or 24-hr post-TBI (FIG. 2d). Thus, delaying DIM treatment for 2-hr caused no falloff in survival. Even when DIM was delayed for 24-hr, survival was still appreciable (30%), suggesting that DIM acts as a radiation mitigator.

Figure 3A:
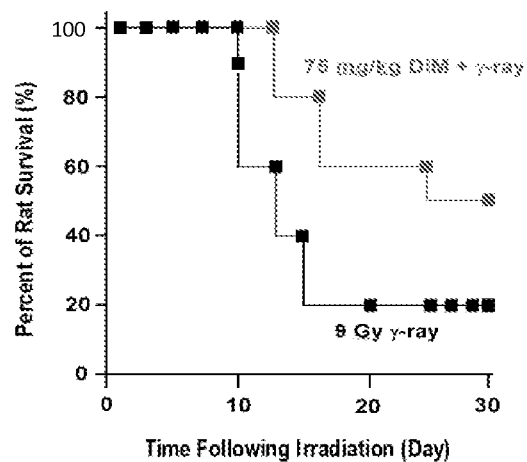
FIGS. 3A, 3B, and 3C show that DIM protects against different doses of total body radiation when administered starting 24-hr after irradiation.
Figure 3B:
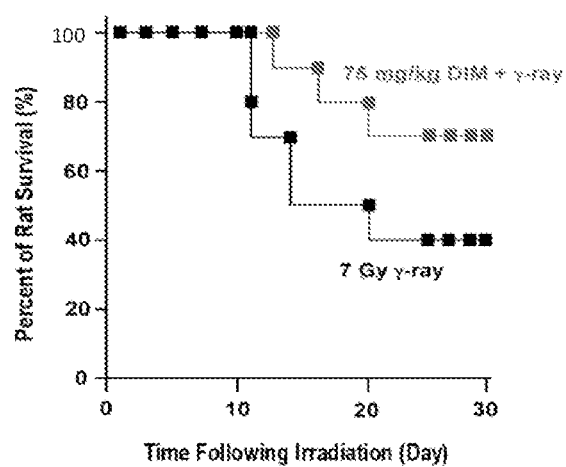
Figure 3C:
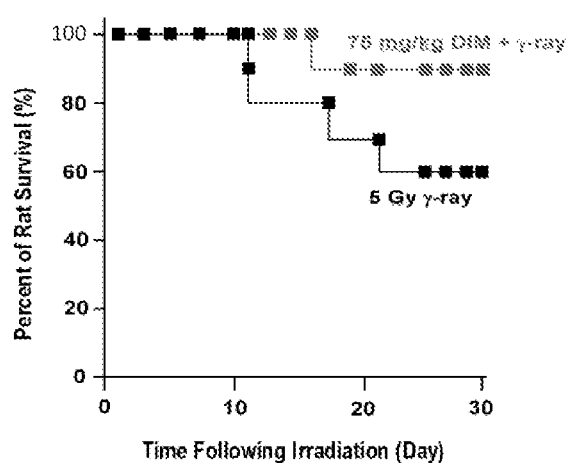

Further studies were performed in SD rats, where DIM (75 mg/kg) was given intraperitoneally for 14-days starting 24-hr post-TBI, using 20 rats per group. The survival rates at 30-days were 60%, 40%, and 20% for vehicle-treated animals at 5, 7, and 9-Gy, respectively, and 90%, 70%, and 50% for DIM-treated rats (see FIG. 3). Taken with the 13-Gy data, the DMF for DIM started 24-hr post-TBI was 1.6.

Figure 4:
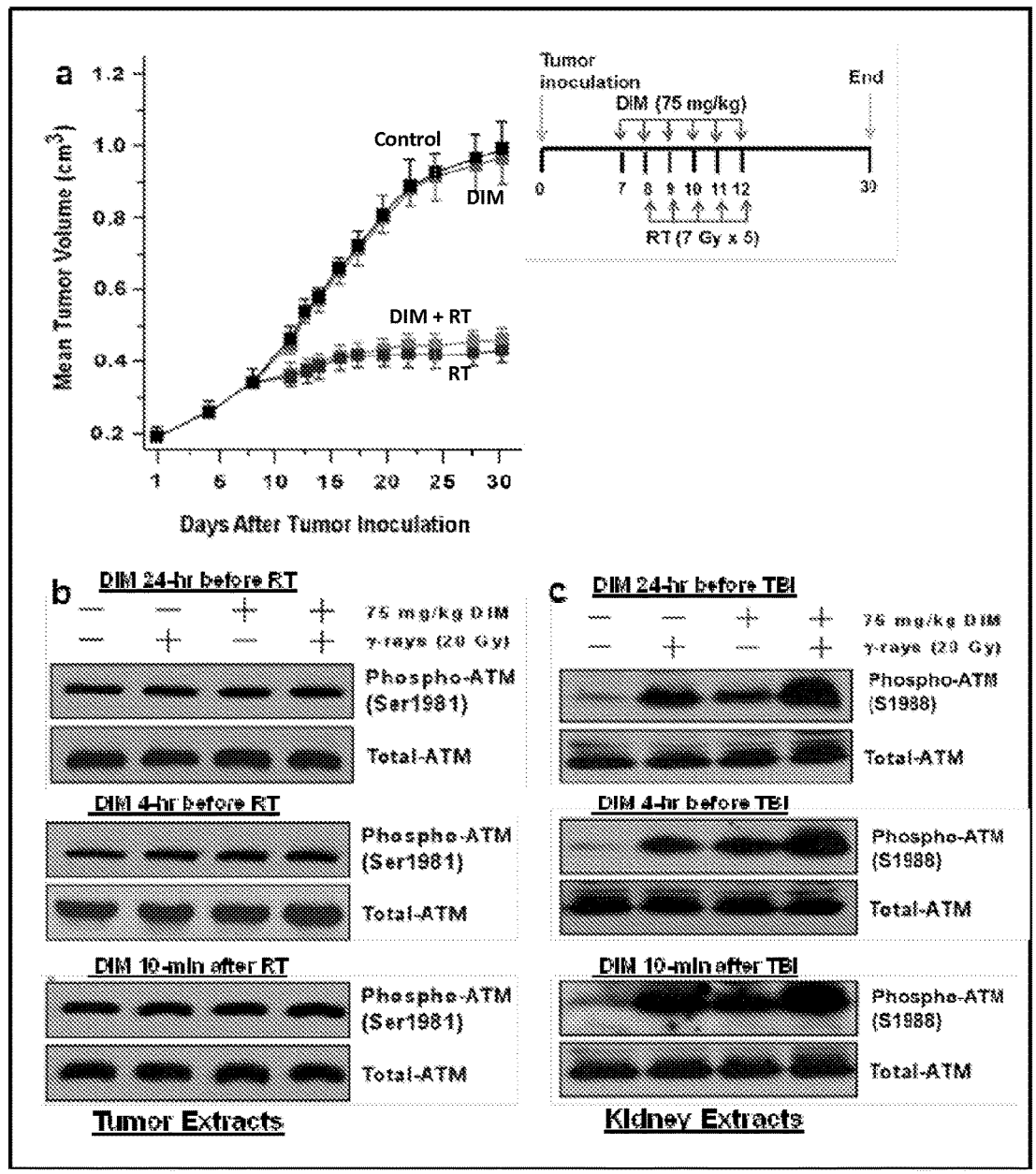
FIG. 4 contains data showing that DIM does not protect MDA-MB-231 tumor xenografts grown in athymic nude mice against fractionated radiation. Panel A shows the tumor sizes in mice after mice were administered the indicated treatment (control=no treatment; DIM; RT=total body irradiation; and DIM+RT). Panel B contains Western blots of athymic nude mice containing MDA-MB-231 xenograft tumors grown in the mammary fat pads treated without (−) or with (+) a single dose of DIM (75 mg/kg) at different times before or after irradiation and then received 20-Gy of γ-rays. Panel C contains Western blots for the mice treated or not treated with DIM (75 mg/kg) at the indicated time before or after total body irradiation (TBI, 20-Gy). S1988 in rat ATM corresponds to S1981 in human ATM.

DIM does not Alter Growth or Radiosensitivity of MDA-MB-231 Breast Cancer Xenografts
  MDA-MB-231 human breast cancer cells were grown as xenograft tumors in the mammary fat pads of athymic nude mice. Starting on day 8 after tumor cell inoculation, the mice were either sham-treated or irradiated using a regimen of 5-daily treatments of 7-Gy each, for a total dose of 35-Gy. Starting one day before irradiation or sham treatment, the mice were given once daily injections of DIM (75 mg/kg) or vehicle for a total of six injections. DIM had no effect on the growth of non-irradiated or irradiated tumors (FIG. 4a). Similar results were observed in a second experiment using a lower dose of radiation (20-Gy in 5-Gy fractions).

DIM Activates ATM in Normal Tissues
  The ability of DIM to activate ATM in vivo was examined utilizing an antibody to phospho-ATM (serine-1981), a marker of ATM activation. As shown in FIG. 4b, ATM was constitutively active (phosphorylated) in MDA-MB-231 tumor tissue extracts and was not further activated in response to DIM alone, radiation alone (20-Gy), or DIM plus radiation. No increases in phospho-ATM levels were observed whether DIM was given 24-hr before, 4-hr before, or 10-min after irradiation. In contrast, in normal mouse kidney tissue, basal phospho-ATM levels were low; and phospho-ATM levels were significantly increased by DIM, radiation (20-Gy), and DIM plus radiation. Phospho-ATM levels were determined 24-hr post irradiation and they appeared to be greater following treatment with DIM plus radiation than either agent alone, suggesting that DIM further activates ATM beyond that due to radiation alone.

Figure 5A:
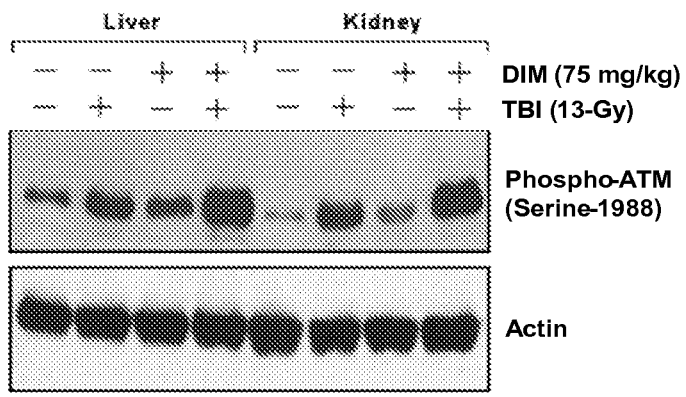
FIG. 5A shows Sprague-Dawley rats treated without (−) or with (+) DIM (75 mg/kg) 24-hr before sham-treatment (−) or TBI (+).
Figure 5B:
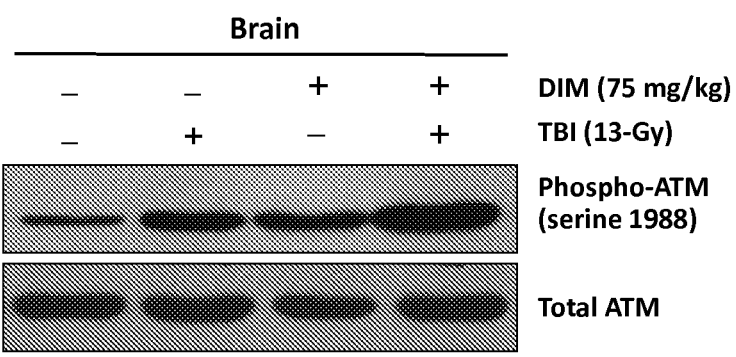
FIG. 5B shows rats treated without (−) or with (+) DIM (75 mg/kg) 1-hr before sham-treatment (−) or TBI (+).
Figure 5C:
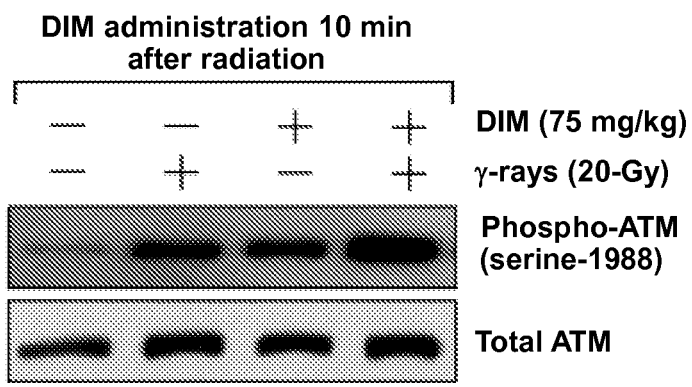
FIG. 5C shows rats sham-treated (−) or treated with TBI (20-Gy) (+) and administered vehicle (−) or DIM (+) at 10-min after radiation. Phospho-ATM (serine-1988) in rat corresponds to phospho-ATM (serine-1981) in humans.

In additional experiments carried out in rats under different conditions, DIM caused ATM phosphorylation by itself and enhanced the radiation-induced phosphorylation in normal rat kidney, liver, and brain (see FIG. 5). Qualitatively similar results were observed in different tissues whether DIM was administered 24-hr before, 1-hr before, or 10-min after irradiation. In all tissues studied, phospho-ATM levels were elevated at 24-hr after TBI, consistent with the idea that radiation causes ongoing oxidative stress in normal tissues, since most double-strand DNA breaks in irradiated cells are repaired within 2-3 hr. The results suggest that DIM can activate ATM and enhance radiation-induced activation in vivo, as a possible mechanism of radioprotection and mitigation.

DIM Radioprotection of Cultured Cells

Significant radioprotection by DIM was observed using MTT assays in which cells were exposed to DIM (0.3 µM) starting 48-hr before radiation to 5-10 min after irradiation. These assays reflect short-term mechanisms of cell death (e.g., apoptosis) and do not allow accurate survival determination below 1.5-2 logs. It was next tested whether DIM could protect cultured cells against radiation using clonogenic survival (colony formation) assays. Cells were exposed to DIM (0.3 µM) for 24-hr, irradiated, and harvested for colony formation assays. FIGS. 6a and 6b show the ability of DIM to protect two non-tumorigenic human mammary epithelial cell lines 184A1 and Hs578Bst. FIGS. 6c and 6d show the effect of DIM concentration on protection, using a single radiation dose (8-Gy). These studies revealed concentration-dependent protection up to 0.3 µM of DIM and additional studies showed further increases in cell survival at higher DIM concentrations up to 3.0 µM, where the protective effect leveled off. Time course studies also revealed that DIM significantly protected cells even when it was administered starting shortly after irradiation.

DIM Stimulates an ATM Signaling Pathway in Cultured Cells

Figure 7A:
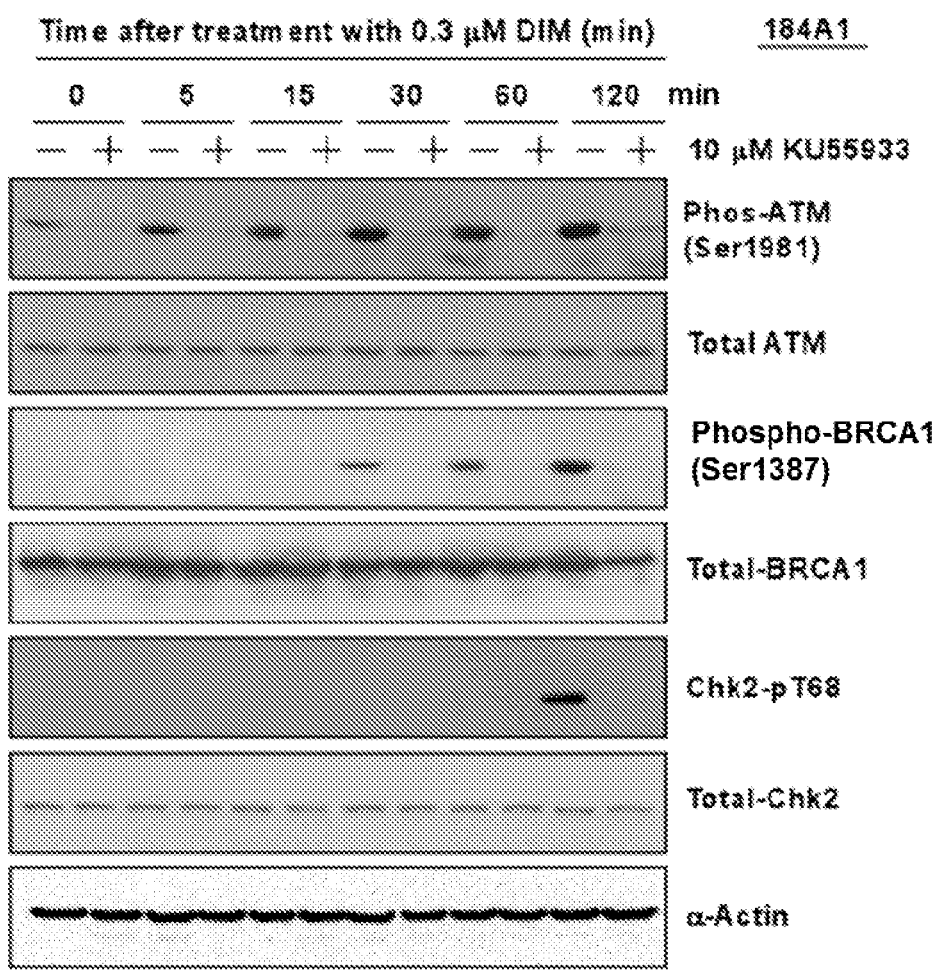
FIG. 7A contains Western blots of subconfluent proliferating 184A1 human mammary epithelial cells exposed to DIM (0.3 μM) for different time intervals. Phosphorylated or total levels of ATM and of several different ATM substrate proteins were determined, as indicated. As a negative control, cells were treated with a selective inhibitor of ATM kinase activity (KU55933).
Figure 7B:
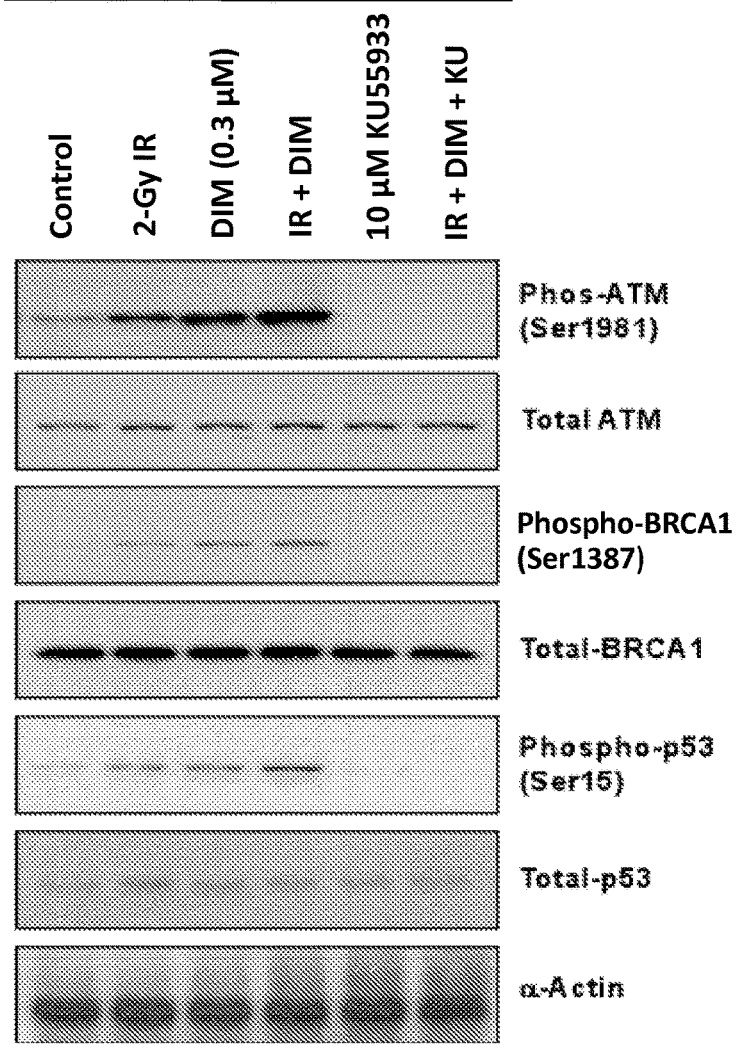
FIG. 7B contains Western blots of 184A1 cells either untreated or treated with radiation (2-Gy of γ-radiation) and/or DIM (0.3 μM).
Figure 8:
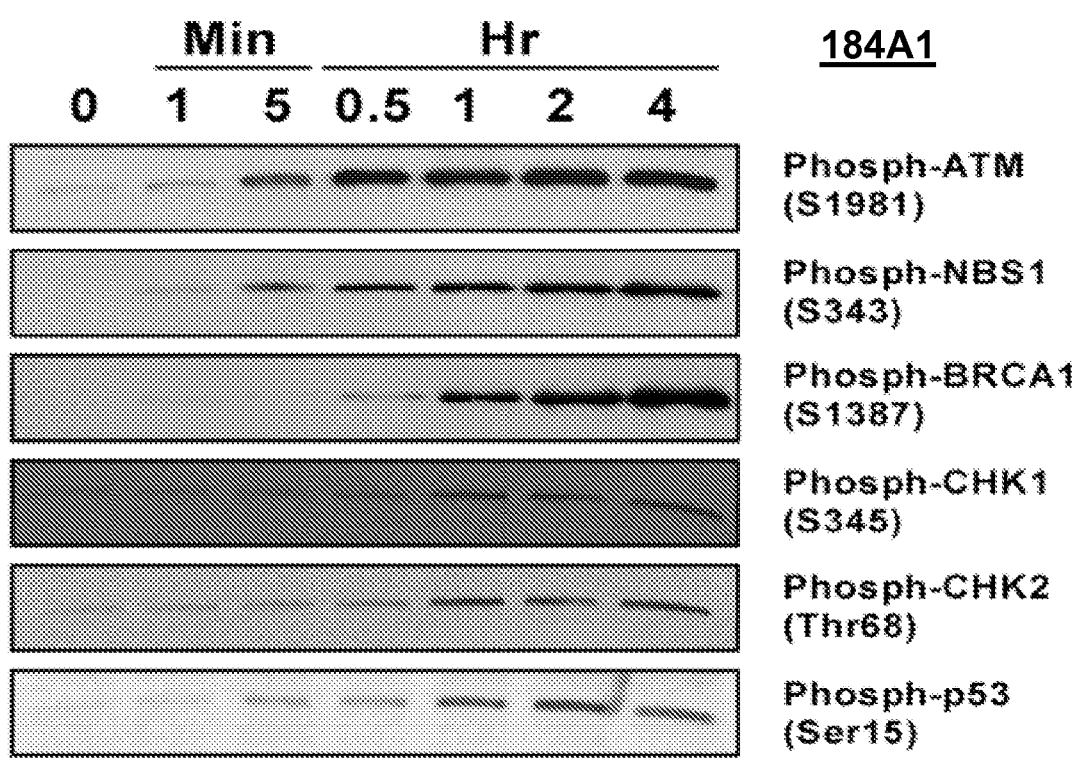
FIG. 8 contains a Western blot of subconfluent proliferating 184A1 human mammary epithelial cells exposed to DIM (0.3 μM) for different time intervals. Phosphorylated or total levels of ATM and of different DNA damage-response proteins were determined, as indicated.

DIM alone (0.3 µM) caused rapid activation of ATM, indicated by phosphorylation on serine-1981 in 184A1 cells (FIG. 7a) and other cell types. Subsequent to ATM, phosphorylation was observed on two ATM substrates (BRCA1 and CHK2) at the ATM sites on these proteins (FIG. 7a). These phosphorylations were blocked by a selective ATM kinase inhibitor (KU55933, 10 µM), suggesting that DIM stimulates an ATM signaling pathway. In a study combining ionizing radiation and DIM (0.3 µM), at 30-min after radiation, the combination of DIM and radiation gave greater phosphorylation of ATM and several substrates than either agent alone (FIG. 7b), suggesting that in the setting of DNA damage, DIM might function to "hyper-activate" ATM. In additional studies, increased phosphorylation of ATM and NBS1, an ATM substrate, was observed after only 1-min of exposure to DIM, followed by phosphorylation of p53, and later BRCA1 and CHK2 on their ATM sites (FIG. 8). DIM also stimulated the phosphorylation of CHK1 on serine-345. CHK1 is a DDR protein for which DNA damage-induced phosphorylation is thought to be mediated primarily by ATR rather than ATM. However, some studies have identified an additional role for ATM in the regulation of CHK2 phosphorylation. Taken together, these findings show that DIM, which does cause DNA damage, can stimulate a DNA damage response (DDR)-like response in cultured cells.

ATM, BRCA1, and MRE11 are Required for Radioprotection

Figure 9:
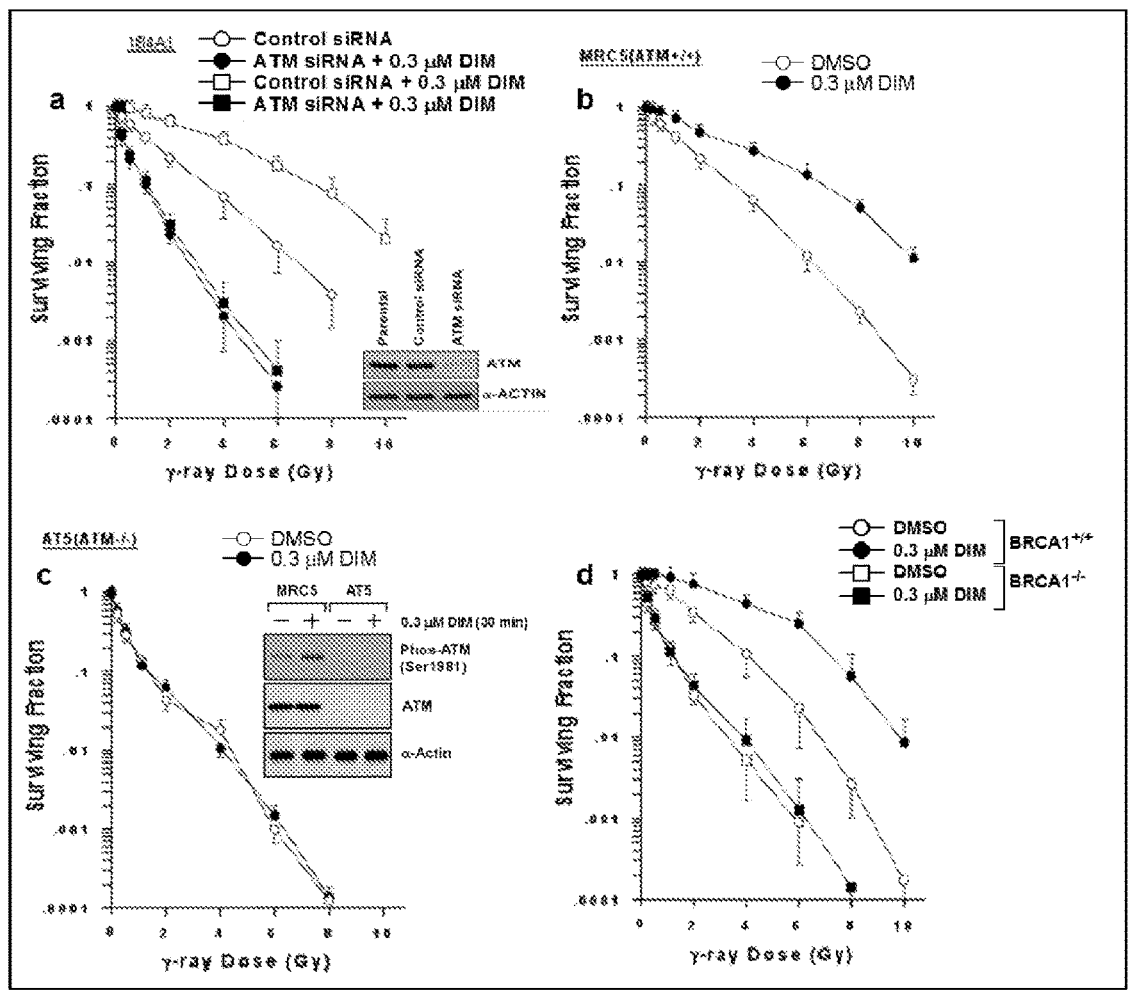
FIG. 9 shows that ATM and BRCA1 are required for radioprotection by DIM. Panel A depicts the clonogenic survival of 184A1 human mammary epithelial cells pre-treated with control-siRNA or ATM-siRNA (50 nM for 48-hr), treated±DIM (0.3 μM) for 24-hr, and irradiated. The extent of knockdown of ATM is shown in the inset Western blot. Panels B and C show the clonogenic survival of ATM-competent (+/+) MRC5 human fibroblasts (Panel B) or ATM mutant (−/−) AT5 human fibroblasts (Panel C) pre-treated±DIM (1 μM) for 24-hr and irradiated. The Western blot inset in Panel C shows the ATM protein levels in MRC5 and AT5 fibroblasts. Panel D shows BRCA1-competent (Brca1+/+) or BRCA1-deficient (Brca1−/−), but otherwise isogenic, mouse embryo fibroblasts pre-treated±DIM (0.3 μM) for 24-hr and then assayed for clonogenic survival in response to radiation.

The ability of DIM to protect ATM-deficient cells against radiation was tested. Knock-down of ATM using siRNA caused marked sensitization of 184A1 cells to radiation, as expected, and abolished DIM-induced radioprotection (FIG. 9a). In contrast, cells treated with control-siRNA showed strong radioprotection by DIM. Using a genetic approach, ATM null (ATM$^{-/-}$) human fibroblasts (AT5 cells, which were derived from an ataxia-telangiectasia patient) were considerably more radiosensitive than control (ATM$^{+/+}$) human fibroblasts (MRC5) and were not protected at all by DIM (FIGS. 9b and 9c). Furthermore, BRCA1$^{-/-}$ mouse embryo fibroblasts were also more sensitive to radiation than BRCA1$^{+/+}$ fibroblasts and were not protected by DIM (FIG. 9d). Taken together, these findings suggest that not only does DIM stimulate ATM signaling but also that an ATM/BRCA1 signaling pathway is required for DIM-mediated protection of cultured cells against ionizing radiation.

Figure 10:
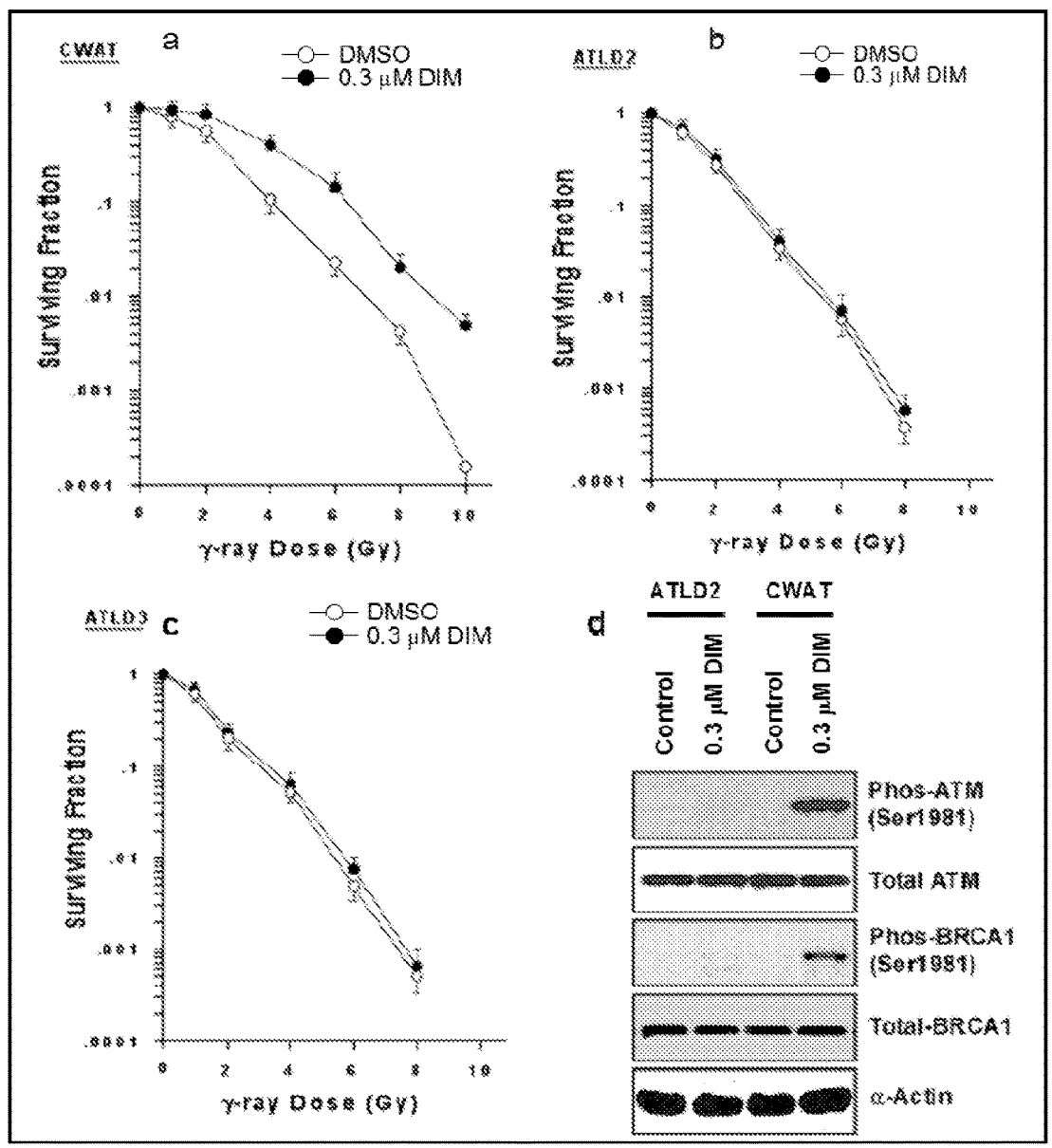
FIG. 10 shows that DIM protects wild-type but not Mre11 mutant human dermal fibroblasts. Panels A, B, and C show subconfluent proliferating wild-type (CWAT) (Panel A) or Mre11 mutant (ATLD2) (Panel B) and ATLD3) (Panel C)) human skin fibroblasts treated with DIM (0.3 μM) or vehicle (DMSO) for 24-hr; irradiated with different doses of $^{137}$Cs γ-rays; and harvested for clonogenic survival assays. Cell survival values are means±SEMs of three replicate dishes. Panel D shows Western blots of wild-type or Mre-11 mutant (ATLD2) fibroblasts treated with DIM (0.3 μM) or vehicle for 30 min and then subjected to Western blotting to detect phospho-ATM (S1981), total ATM, phospho-BRCA1 (S1387), total BRCA1, or actin (loading control).

MRE11 is a component of the "MRN" (MRE11-RAD50-NBS1) complex, which is thought to act as a DNA damage sensor and up-stream activator of ATM. Individuals with MRE11 mutations exhibit an ataxia-telangiectasia-like disorder (ATLD) similar to those with inherited ATM mutations. Whereas wild-type human dermal fibroblasts (CWAT) exhibited protection by DIM (0.3 µM), MRE11-deficient cell lines (ATLD2 and ATLD3) were more radiosensitive than CWAT and were not protected by DIM (FIG. 10a-c). In contrast to wild-type fibroblasts (CWAT), MRE11-deficient cells (ATLD2) showed no DIM-induced phosphorylation of ATM or BRCA1 after a 30 min exposure to DIM. These findings suggest that in addition to ATM and BRCA1, MRE11 is also required for DIM-mediated radioprotection.

DIM Stimulates DNA Repair and Inhibits Apoptosis

Figure 11A:
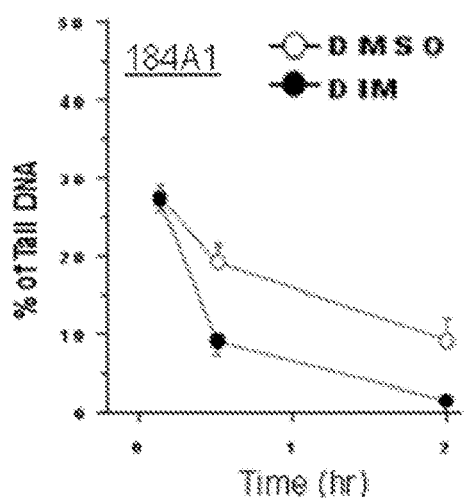
FIGS. 11A and 11B show subconfluent proliferating 184A1 (FIG. 11A) or Hs578Bst (FIG. 11B) cells pre-treated±DIM (0.3 μM×24 hr); exposed to radiation (3-Gy) on ice; and subjected to neutral comet assays at different times post-irradiation. Values of % tail DNA are means±ranges of two determinations.
Figure 11B:
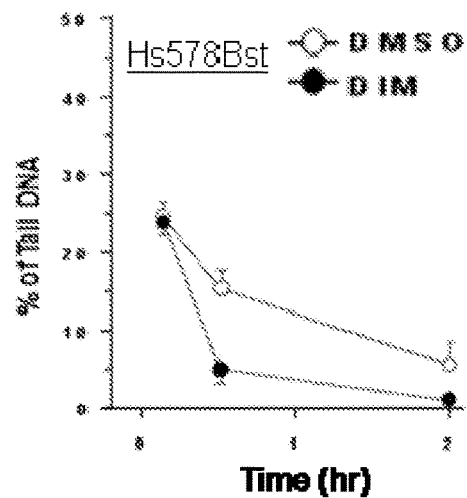
Figure 11C:
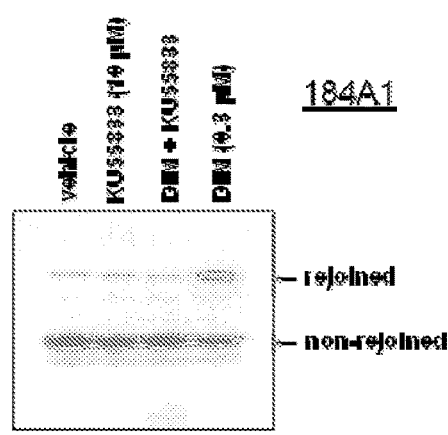
FIG. 11C shows plasmid strand-rejoining assays carried out using 75 μg of nuclear lysates from 184A1 cells that were treated with DIM (0.3 μM) or vehicle (DMSO) for 24-hr with and without ATM kinase inhibitor KU55933 (10 μM).

Since ATM is known to have a major role in the repair of radiation-induced double-strand breaks (DSBs) of DNA, it was tested whether DIM could stimulate the repair of DSBs. The neutral comet assay is an electrophoretic method to measure DNA damage that reflects DSBs. The percent of tail DNA after irradiation reflects the number of DSBs. Pre-treatment with DIM (0.3 µM) for 24-hr reduced the % of comet tail DNA (reflecting DSBs) at 30-min and 2-hr post radiation (3-Gy), suggesting more rapid DNA repair (FIGS. 11a and 11b). A DNA strand-rejoining assay based on the ability of cell nuclei to rejoin a linearized plasmid (pEGFP-1) was also performed, detected by Southern blotting. This assay reflects the process of non-homologous end joining (NEHJ). In FIG. 11c, nuclear extracts of vehicle-treated cells showed a modest ability to rejoin DNA strands that was greatly enhanced by pre-treatment with DIM. KU55833 blocked DIM-induced strand-rejoining, suggesting it is ATM-dependent. In various cell types, control cells gave 0-2% strand-rejoining and DIM-treated cells showed 40-60% rejoining.

Figure 11D:
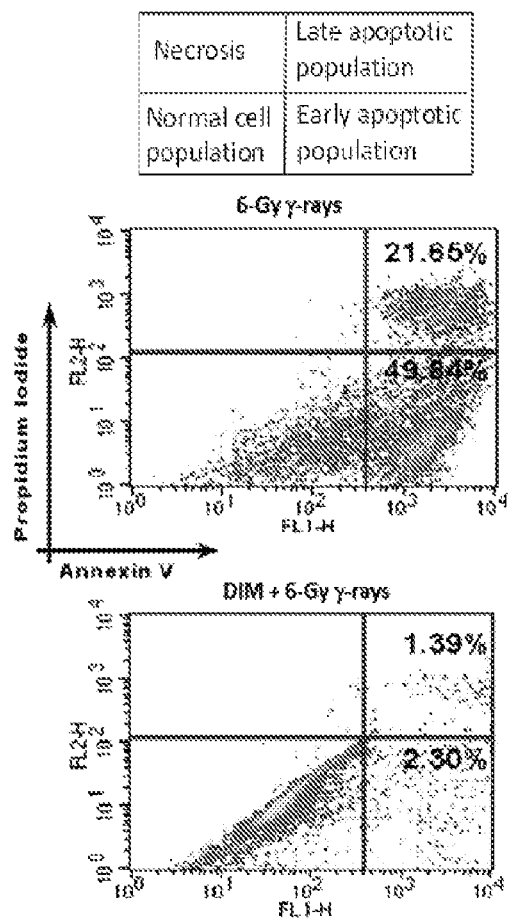
FIG. 11D shows the apoptosis assays of 184A1 cells pre-treated±DIM (0.3 μM) for 24-hr and irradiated with 6-Gy of γ-rays. At 24-hr after irradiation, cells were analyzed by flow cytometry for apoptosis, by measuring membrane redistribution of phosphatidylserine. The percentage of early and late apoptotic cells for non-irradiated control cells were: vehicle treated, 1.25% and 1.34%, and DIM-treated, 0.54% and 1.02%, respectively.

Pre-treatment with DIM for 24-hr blocked radiation-induced apoptosis in 184A1 cells, as determined by flow cytometry of annexin V-labeled cells (FIG. 11d). The anti-apoptotic effect of DIM could also reflect ATM signaling, since ATM is known to stimulate anti-apoptotic pathways (eg., NF-κB) in irradiated cells.

Example 3: Radioprotector Compounds

Figure 6:
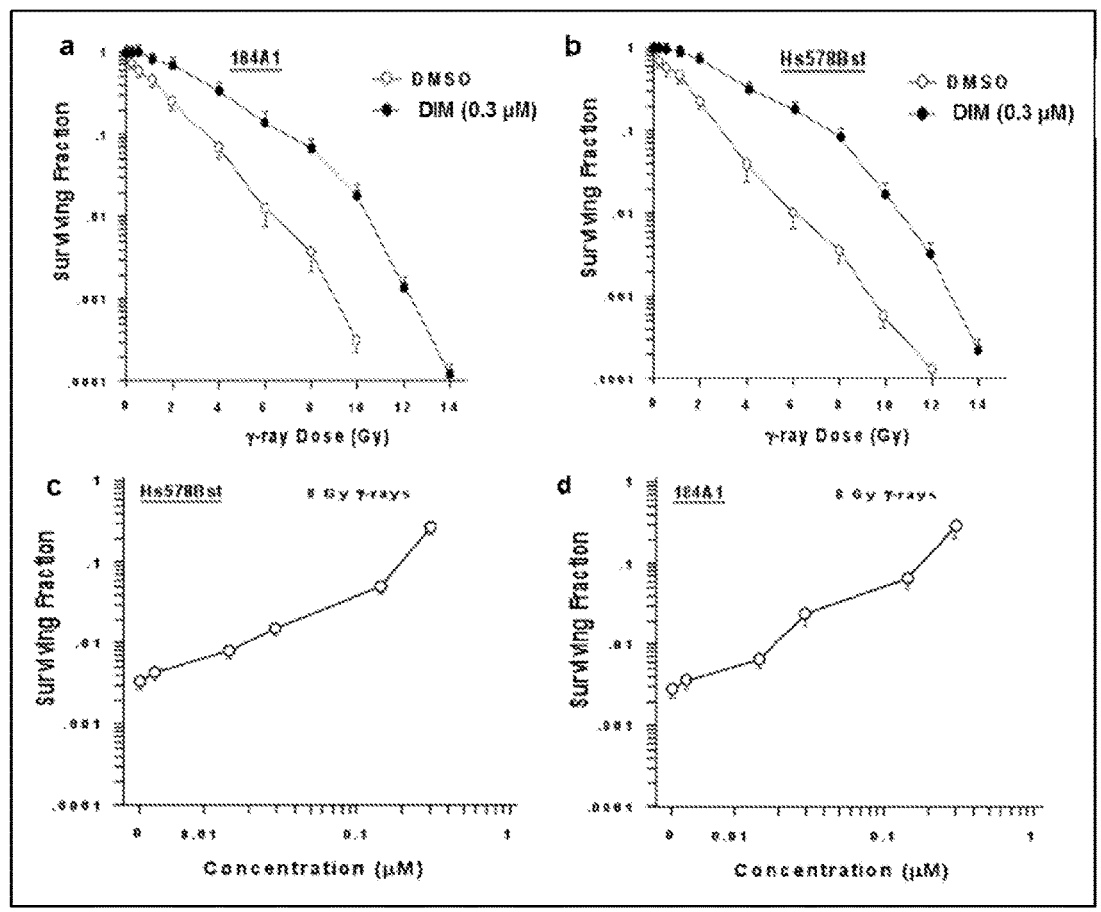
FIG. 6 contains graphs demonstrating the radioprotection of cultured human cells by DIM. Panels A and B show the surviving fraction of subconfluent proliferating cultures of 184A1 (Panel A) and Hs578Bst (Panel B) cells pre-treated with DIM (0.3 μM) or vehicle (DMSO) for 24-hr and irradiated using different doses of γ-rays. Panels C and D show the concentration dependence of DIM radioprotection on clonogenic survival of 184A1 (Panel C) and Hs578Bst (Panel D) cells using a single dose of radiation (8-Gy) and different concentrations of DIM.

Novel compounds were synthesized, which we have tested for their ability to protect cells against radiation in cultured cells. Some of these compounds gave strong levels of radiation protection similar to, slightly greater than, or slightly less than DIM, including compounds KED-4-157, KED-4-155, KED-4-159, KED-4-153, KED-4-123, KED-4-46, THW-5-85, and KED-4-69. None of these compounds are predicted to be free-radical scavengers or to be genotoxic. For reference, clonogenic radiation survival curves of cultured human mammary epithelial cells treated without or with DIM are shown in FIG. 6, panels A and B. In these studies, human mammary epithelial cells at about 70-80% of confluency were treated with DIM (0.3 µM) or vehicle (DMSA) for 24 hours. The cells were then irradiated using different doses of $^{137}Cs$ gamma rays, harvested, plated at different densities in the presence of DIM (0.3 µM) or vehicle, respectively, incubated for 14 days, and then counted for colony formation. In FIG. 6, panels A and B, the clonogenic survival curves are shown using non-tumorigenic human mammary epithelial cell lines Hs5788st (panel B) or 184A1 (panel A). All cell survival values are means±SEMs of three replicate dishes.

Figure 12:
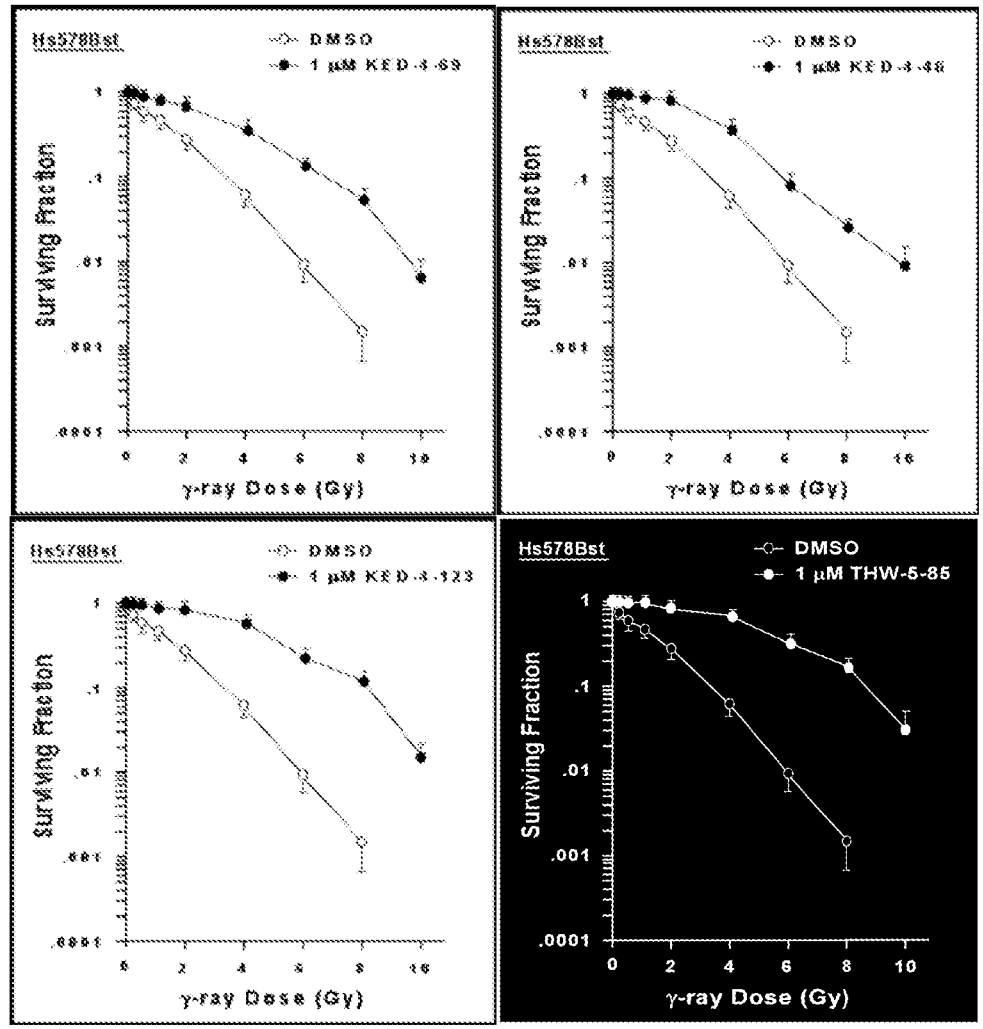
FIG. 12 contains graphs depicting the clonogenic survival curves of non-tumorigenic human mammary epithelial cell lines Hs5788st after different doses of gamma ray irradiation, with and without KED-4-69 treatment (top left panel), KED-4-46 treatment (top right panel), KED-4-123 treatment (bottom left panel), and THW-5-85 treatment (bottom right panel).

Radiation dose-response curves for the same cell type treated with different DIM-related analogs are shown in FIG. 12. Cells at about 70-80% confluency were treated with vehicle (DMSO) or with the indicated compound (1 µM) for 24 hours, irradiated using different doses of $^{137}Cs$ gamma rays, harvested, plated at different densities in the presence of the compound (0.3 µM) or vehicle, respectively, incubated for 14 days, and then counted for colony formation. In FIG. 12, clonogenic survival curves are shown using non-tumorigenic human mammary epithelial cell line Hs578Bst. All cell survival values are means±SEMs of three replicate dishes. Like DIM, these analogs gave strong radiation protection, with fold-increases in survival in the range of (20-100)-fold at different doses of radiation.

Figure 13:
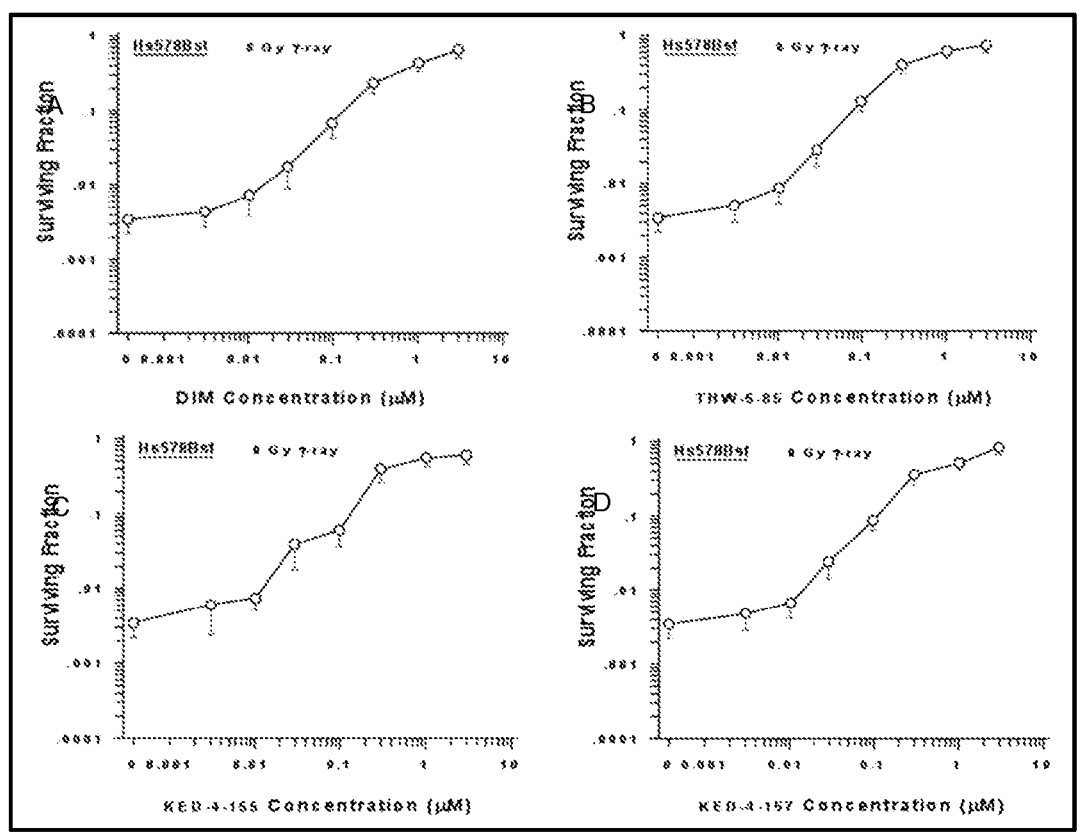
FIG. 13 contains graphs depicting the clonogenic survival curves of non-tumorigenic human mammary epithelial cell lines Hs5788st after a single dose of gamma ray irradiation, with and without DIM treatment (panel A; top left panel), THW-5-85 treatment (panel B; top right panel), KED-4-155 treatment (panel C; bottom left panel), and KED-4-157 treatment (panel D; bottom right panel).

A comparison of the survival enhancing effects of DIM against three different compounds is shown in FIG. 13. A single dose of radiation (8-Gy) was used and different concentrations of DIM (panel A), THW-5-85 (panel B), KED-4-155 (panel C), or KED-4-157 (panel D). Each analog was at least as potent as DIM at the different concentrations tested. Some analogs gave greater protection at some concentrations. Taken together, these findings show that new classes of small molecule drug-like compounds related to DIM as the prototype have been discovered that act as potent radiation protectors. DIM and the synthesized compounds protect a variety of different cell types against radiation.

The mechanism of radiation protection is similar to that of DIM, but these compounds could also have other effects that are independent of DIM. A combination of two of these agents (THW-5-85 plus KED-4-157) gave considerably greater radiation protection than did either agent alone and also gave considerably greater radiation protection than did DIM, showing combination therapy may be more beneficial than single agent therapy. These agents are of interest because they have the potential to make superior radioprotectors and mitigators to DIM. Although when used as single agents in cultured cells, the degree of protection is similar to that afforded by DIM, in combination they are superior to DIM. Importantly, when used in animals or humans, DIM is still limited by its bioavailability. Thus, an agent that is significantly more bioavailable than absorption enhanced DIM (BR-DIM) makes a superior radioprotector and/or radiation mitigator in animals and humans even though at the cellular level it is only as good as DIM.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims.

Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A compound of the following structure:

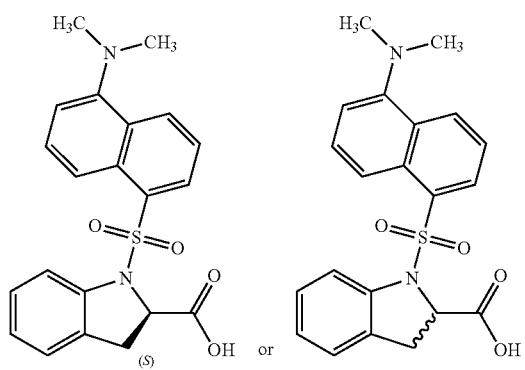

or a pharmaceutically acceptable salt or prodrug thereof.

2. A composition comprising one or more of the compounds according to claim 1 and a pharmaceutically acceptable carrier.

3. A method of reducing radiation damage in a subject, comprising:
    administering to the subject an effective amount of the compound of claim 1.

4. The method of claim 3, further comprising administering a second therapeutic agent to the subject, wherein the second therapeutic agent is 3,3'-diindolylmethane (DIM).

5. A method of killing a breast cancer tumor cell or an ovarian cancer tumor cell and protecting a non-tumor cell, comprising:
    irradiating the tumor cell with an effective amount of ionizing radiation; and
    administering to the non-tumor cell an effective amount of the compound of claim 1.

6. The method of claim 5, wherein the irradiating step is performed prior to the administering step or wherein the administering step is performed prior to the irradiating step.

7. The method of claim 5, wherein the tumor cell is a $BRCA_1$-deficient tumor cell.

8. A method of treating breast cancer or ovarian cancer in a subject, comprising:
    administering to the subject an effective amount of ionizing radiation; and
    administering to the subject an effective amount of the compound of claim 1.

9. The method of claim 8, wherein the breast cancer is $BRCA_1$-deficient breast cancer.

10. The method of claim 8, wherein the ovarian cancer is $BRCA_1$-deficient ovarian cancer.

11. The compound of claim 1, wherein the compound is
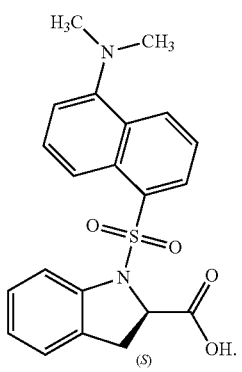
12. The method of claim 3, wherein the compound is
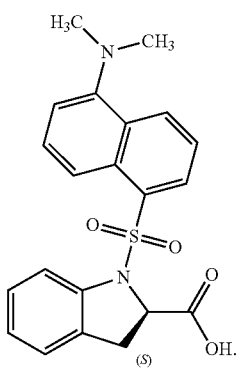
13. The method of claim 5, wherein the compound is
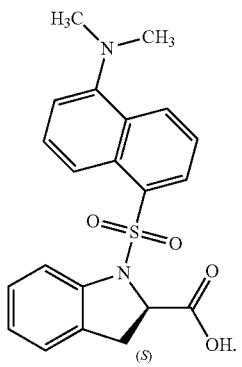
14. The method of claim 8, wherein the compound is
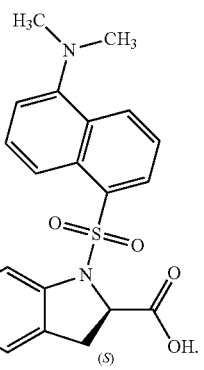
* * * * *